(12) United States Patent
Lin et al.

(10) Patent No.: US 9,933,385 B2
(45) Date of Patent: Apr. 3, 2018

(54) METHOD OF USING AN ELECTROCHEMICAL TEST SENSOR

(71) Applicant: Bayer HealthCare LLC, Whippany, NJ (US)

(72) Inventors: Jing Lin, Belmont, MA (US); Fu Hsiung Tsai, San Diego, CA (US); Huan-Ping Wu, Granger, IN (US); Nicole D Ellis, Mishawaka, IN (US); Henry C Arndt, Elkhart, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 649 days.

(21) Appl. No.: 14/491,272

(22) Filed: Sep. 19, 2014

(65) Prior Publication Data

US 2015/0008143 A1 Jan. 8, 2015

Related U.S. Application Data

(60) Division of application No. 14/105,839, filed on Dec. 13, 2013, now Pat. No. 8,871,517, which is a
(Continued)

(51) Int. Cl.
*G01N 27/26* (2006.01)
*G01N 27/327* (2006.01)
(Continued)

(52) U.S. Cl.
CPC ............. *G01N 27/26* (2013.01); *C12Q 1/001* (2013.01); *G01N 27/327* (2013.01);
(Continued)

(58) Field of Classification Search
CPC .. G01N 27/3274; G01N 27/327; G01N 27/26; G01N 33/96; G01N 33/66;
(Continued)

(56) References Cited

U.S. PATENT DOCUMENTS 3,167,651 A  1/1965 Huett et al.
3,420,205 A  1/1969 Morrison
(Continued)

FOREIGN PATENT DOCUMENTS

CA  2423837  10/2000
CA  2358993  5/2001
(Continued)

OTHER PUBLICATIONS

Dalrymple-Alford, P., et al., "Peak Shapes in Semi-differential Electroanalysis", "Anal. Chem.", 1977, pp. 1390-1394, vol. 49, No. 9, Publisher: American Chemical Society, Published in: USA.
(Continued)

*Primary Examiner* — Gurpreet Kaur
(74) *Attorney, Agent, or Firm* — Nixon Peabody LLP

(57) ABSTRACT

A method of distinguishing a control solution from a sample in an electrochemical test sensor is performed. The method includes adding a control marker to the control solution. The control solution includes the control marker and analyte. The test sensor includes working and counter electrodes, and a reagent. A potential is applied to the test sensor to oxidize the control marker and the analyte. The resulting electrical current is measured. A potential is applied to the test sensor lower than the other potential in which the potential is sufficient to oxidize the analyte and not the control marker. The resulting electrical current is measured. Determining whether a control solution or a sample is present based on the measured electrical currents. To increase the measured current, a salt may be added to the control solution in an amount sufficient to increase the electrical current by at least 5% as compared to a control solution in the absence of a salt.

8 Claims, 12 Drawing Sheets

Related U.S. Application Data continuation of application No. 13/682,380, filed on Nov. 20, 2012, now Pat. No. 8,716,024, which is a division of application No. 12/316,133, filed on Dec. 10, 2008, now Pat. No. 8,337,691.

(60) Provisional application No. 61/007,211, filed on Dec. 10, 2007.

(51) Int. Cl.
    *C12Q 1/00* (2006.01)
    *G01N 33/96* (2006.01)
    *G01N 33/66* (2006.01)

(52) U.S. Cl.
    CPC ......... *G01N 27/3274* (2013.01); *G01N 33/66* (2013.01); *G01N 33/96* (2013.01); *G01N 2496/00* (2013.01); *Y10T 436/10* (2015.01); *Y10T 436/104998* (2015.01); *Y10T 436/13* (2015.01); *Y10T 436/144444* (2015.01)

(58) Field of Classification Search
    CPC ......... Y10T 436/10; Y10T 436/104998; Y10T 436/13; C12Q 1/001
    See application file for complete search history.

(56) References Cited

U.S. PATENT DOCUMENTS

| | | | |
|---|---|---|---|
| 3,505,136 | A | 4/1970 | Attwood |
| 3,510,268 | A | 5/1970 | Hach |
| 3,551,295 | A | 12/1970 | Dyer |
| 3,562,041 | A | 2/1971 | Robertson |
| 3,573,139 | A | 3/1971 | Mori et al. |
| 3,621,381 | A | 11/1971 | Eckfeldt |
| 3,715,192 | A | 2/1973 | Wenz et al. |
| 3,720,093 | A | 3/1973 | Gill |
| 3,763,422 | A | 10/1973 | MacPhee et al. |
| 3,770,607 | A | 11/1973 | Williams |
| 3,776,832 | A | 12/1973 | Oswin et al. |
| 3,791,933 | A | 2/1974 | Wenz et al. |
| 3,791,988 | A | 2/1974 | Bauer et al. |
| 3,806,718 | A | 4/1974 | Stewart |
| 3,838,033 | A | 9/1974 | Mindt et al. |
| 3,902,970 | A | 9/1975 | Levin |
| 3,917,453 | A | 11/1975 | Milligan et al. |
| 3,919,627 | A | 11/1975 | Allen |
| 3,920,580 | A | 11/1975 | Mast |
| 3,925,183 | A | 12/1975 | Oswin et al. |
| 3,937,615 | A | 2/1976 | Clack et al. |
| 3,948,745 | A | 4/1976 | Guillbault et al. |
| 3,952,183 | A | 4/1976 | Abe |
| 3,980,437 | A | 9/1976 | Kishimoto et al. |
| 4,005,002 | A | 1/1977 | Racine et al. |
| 4,008,448 | A | 2/1977 | Muggli |
| 4,040,908 | A | 8/1977 | Clark, Jr. |
| 4,053,381 | A | 10/1977 | Hamblen et al. |
| 4,065,263 | A | 12/1977 | Woodbridge et al. |
| 4,077,861 | A | 3/1978 | Lauer |
| 4,123,701 | A | 10/1978 | Josefsen et al. |
| 4,127,448 | A | 11/1978 | Schick et al. |
| 4,137,495 | A | 1/1979 | Brown |
| 4,184,936 | A | 1/1980 | Paul et al. |
| 4,214,968 | A | 7/1980 | Battaglia et al. |
| 4,217,196 | A | 8/1980 | Huch |
| 4,224,125 | A | 9/1980 | Nakamura et al. |
| 4,225,410 | A | 9/1980 | Pace et al. |
| 4,229,426 | A | 10/1980 | Haagensen, Jr. |
| 4,230,537 | A | 10/1980 | Delente et al. |
| 4,233,029 | A | 11/1980 | Columbus |
| 4,260,680 | A | 4/1981 | Muramatsu et al. |
| 4,263,343 | A | 4/1981 | Kim |
| 4,265,250 | A | 5/1981 | Parker |
| 4,273,639 | A | 5/1981 | Gottermeier |
| 4,297,184 | A | 10/1981 | Dyer |
| 4,297,569 | A | 10/1981 | Flies |
| 4,301,412 | A | 11/1981 | Hill et al. |
| 4,303,887 | A | 12/1981 | Hill et al. |
| 4,304,853 | A | 12/1981 | Jozefonvicz et al. |
| 4,323,536 | A | 4/1982 | Columbus |
| 4,329,642 | A | 5/1982 | Luthi et al. |
| 4,366,033 | A | 12/1982 | Richter et al. |
| 4,376,689 | A | 3/1983 | Nakamura et al. |
| 4,381,775 | A | 5/1983 | Nose et al. |
| 4,396,464 | A | 8/1983 | Giner et al. |
| 4,402,940 | A | 9/1983 | Nose et al. |
| 4,403,984 | A | 9/1983 | Ash et al. |
| 4,407,290 | A | 10/1983 | Wiber |
| 4,407,959 | A | 10/1983 | Tsuji et al. |
| 4,413,407 | A | 11/1983 | Columbus |
| 4,420,564 | A | 12/1983 | Tsuji et al. |
| 4,431,004 | A | 2/1984 | Bessman et al. |
| 4,436,094 | A | 3/1984 | Cerami |
| 4,440,175 | A | 4/1984 | Wilkins |
| 4,473,457 | A | 9/1984 | Columbus |
| 4,476,149 | A | 10/1984 | Poppe et al. |
| 4,477,314 | A | 10/1984 | Richter et al. |
| 4,490,216 | A | 12/1984 | McConnell |
| 4,499,423 | A | 2/1985 | Matthiessen |
| 4,502,938 | A | 3/1985 | Covington et al. |
| 4,517,291 | A | 5/1985 | Seago |
| 4,545,382 | A | 10/1985 | Higgins et al. |
| 4,547,735 | A | 10/1985 | Kiesewetter et al. |
| 4,552,458 | A | 11/1985 | Lowne |
| 4,561,944 | A | 12/1985 | Sasaki et al. |
| 4,571,292 | A | 2/1986 | Liu et al. |
| 4,572,899 | A | 2/1986 | Walker et al. |
| 4,578,716 | A | 3/1986 | Van Rijckevorsel et al. |
| 4,579,893 | A | 4/1986 | Wang et al. |
| 4,582,684 | A | 4/1986 | Vogel et al. |
| 4,592,893 | A | 4/1986 | Wang et al. |
| 4,591,550 | A | 5/1986 | Hafeman et al. |
| 4,628,193 | A | 12/1986 | Blum |
| 4,642,295 | A | 2/1987 | Baker |
| 4,648,665 | A | 3/1987 | Davis et al. |
| 4,652,830 | A | 3/1987 | Brown |
| 4,654,197 | A | 3/1987 | Lilja et al. |
| 4,671,288 | A | 5/1987 | Gough |
| 4,676,653 | A | 5/1987 | Strohmeier et al. |
| 4,679,532 | A | 7/1987 | Luksha |
| 4,680,268 | A | 7/1987 | Clark, Jr. |
| 4,682,602 | A | 7/1987 | Prohaska |
| 4,686,479 | A | 8/1987 | Young et al. |
| 4,703,017 | A | 10/1987 | Campbell et al. |
| 4,703,756 | A | 11/1987 | Gough et al. |
| 4,713,347 | A | 12/1987 | Mitchell et al. |
| 4,714,874 | A | 12/1987 | Morris et al. |
| 4,721,677 | A | 1/1988 | Clark, Jr. |
| 4,729,959 | A | 3/1988 | Ryan |
| 4,731,726 | A | 3/1988 | Allen et al. |
| 4,734,184 | A | 3/1988 | Burleigh et al. |
| 4,745,076 | A | 5/1988 | Muller et al. |
| 4,746,607 | A | 5/1988 | Mura et al. |
| 4,750,496 | A | 6/1988 | Reinhart et al. |
| 4,759,828 | A | 7/1988 | Young et al. |
| 4,775,575 | A | 10/1988 | Tang |
| 4,795,542 | A | 1/1989 | Ross et al. |
| 4,797,256 | A | 1/1989 | Watlington, IV |
| 4,805,624 | A | 2/1989 | Yao et al. |
| 4,806,311 | A | 2/1989 | Greenquist |
| 4,806,312 | A | 2/1989 | Greenquist |
| 4,810,203 | A | 3/1989 | Komatsu |
| 4,816,224 | A | 3/1989 | Vogel et al. |
| 4,820,399 | A | 4/1989 | Senda et al. |
| 4,820,636 | A | 4/1989 | Hill et al. |
| 4,830,595 | A | 5/1989 | McNeil et al. |
| 4,832,814 | A | 5/1989 | Root |
| 4,834,234 | A | 5/1989 | Sacherer et al. |
| 4,849,330 | A | 7/1989 | Humphries et al. |
| 4,854,153 | A | 8/1989 | Miyagawa et al. |
| 4,865,873 | A | 9/1989 | Cole, Jr. et al. |
| 4,877,580 | A | 10/1989 | Aronowitz et al. |
| 4,890,926 | A | 1/1990 | Dosmann et al. |
| 4,894,137 | A | 1/1990 | Takizawa et al. |

(56) References Cited

U.S. PATENT DOCUMENTS

| | | |
|---|---|---|
| 4,897,162 A | 1/1990 | Lewandoski et al. |
| 4,919,770 A | 4/1990 | Preidel et al. |
| 4,927,516 A | 5/1990 | Yamaqucji et al. |
| 4,929,330 A | 5/1990 | Osaka et al. |
| 4,929,545 A | 5/1990 | Freitage |
| 4,935,105 A | 6/1990 | Churchouse |
| 4,935,106 A | 6/1990 | Beach, Jr. et al. |
| 4,935,346 A | 6/1990 | Kugler |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,963,814 A | 10/1990 | Parks et al. |
| 4,970,145 A | 11/1990 | Bennetto et al. |
| 4,975,647 A | 12/1990 | Downer et al. |
| 4,976,724 A | 12/1990 | Nieto |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,028,542 A | 7/1991 | Kennamer et al. |
| 5,035,862 A | 7/1991 | Dietze et al. |
| 5,039,618 A | 8/1991 | Stone |
| 5,046,618 A | 9/1991 | Wood |
| 5,049,487 A | 9/1991 | Phillips et al. |
| 5,057,477 A | 10/1991 | Paterson et al. |
| 5,059,199 A | 10/1991 | Okada et al. |
| 5,059,394 A | 10/1991 | Phillips et al. |
| 5,066,372 A | 11/1991 | Weetall |
| 5,075,077 A | 12/1991 | Durley, III et al. |
| 5,096,669 A | 3/1992 | Lauks et al. |
| 5,096,671 A | 3/1992 | Kane et al. |
| 5,108,819 A | 4/1992 | Heller et al. |
| 5,112,455 A | 5/1992 | Cozzette et al. |
| 5,112,758 A | 5/1992 | Fellman et al. |
| 5,120,421 A | 5/1992 | Glass et al. |
| 5,118,183 A | 6/1992 | Cargill et al. |
| 5,120,420 A | 6/1992 | Nankai et al. |
| 5,122,244 A | 6/1992 | Hoenes et al. |
| 5,140,176 A | 8/1992 | Okino |
| 5,141,850 A | 8/1992 | Cole et al. |
| 5,141,868 A | 8/1992 | Shanks et al. |
| 5,143,694 A | 9/1992 | Schafer et al. |
| 5,155,628 A | 10/1992 | Dosmann |
| 5,179,005 A | 1/1993 | Phillips et al. |
| 5,179,288 A | 1/1993 | Miffitt et al. |
| 5,182,707 A | 1/1993 | Cooper et al. |
| 5,187,100 A | 2/1993 | Matzinger et al. |
| 5,192,415 A | 3/1993 | Yosioka et al. |
| 5,202,261 A | 4/1993 | Musho et al. |
| 5,217,594 A | 5/1993 | Henkens et al. |
| 5,220,920 A | 6/1993 | Gharib |
| 5,223,117 A | 6/1993 | Wrighton et al. |
| 5,229,282 A | 7/1993 | Yoshioka et al. |
| 5,232,516 A | 8/1993 | Hed |
| 5,232,667 A | 8/1993 | Hieb et al. |
| 5,232,668 A | 8/1993 | Grante et al. |
| 5,234,813 A | 8/1993 | MeGreenhan et al. |
| 5,243,516 A | 9/1993 | White |
| 5,246,858 A | 9/1993 | Arbuckle et al. |
| 5,250,439 A | 10/1993 | Mucho et al. |
| 5,261,411 A | 11/1993 | Hughes et al. |
| 5,264,103 A | 11/1993 | Yoshioka et al. |
| 5,266,179 A | 11/1993 | Nanki et al. |
| 5,269,891 A | 12/1993 | Colin |
| 5,279,294 A | 1/1994 | Anderson et al. |
| 5,281,395 A | 1/1994 | Markart et al. |
| 5,282,950 A | 2/1994 | Dietze et al. |
| 5,284,770 A | 2/1994 | Adrain et al. |
| 5,286,362 A | 2/1994 | Hoenes et al. |
| 5,304,468 A | 4/1994 | Phillips et al. |
| 5,306,623 A | 4/1994 | Kiser et al. |
| 5,311,426 A | 5/1994 | Donohue et al. |
| 5,312,590 A | 5/1994 | Gunasingham |
| 5,320,732 A | 6/1994 | Nankai et al. |
| 5,321,492 A | 6/1994 | Detwiler et al. |
| 5,332,479 A | 7/1994 | Uenoyama et al. |
| 5,334,296 A | 8/1994 | Henkens et al. |
| 5,344,754 A | 9/1994 | Zewing |
| 5,352,351 A | 10/1994 | White et al. |
| 5,353,351 A | 10/1994 | Bartoli et al. |
| 5,354,447 A | 10/1994 | Uenoyama et al. |
| 5,361,314 A | 11/1994 | Kopelman et al. |
| 5,366,609 A | 11/1994 | White et al. |
| 5,368,707 A | 11/1994 | Henkens et al. |
| 5,371,687 A | 12/1994 | Holmes, II et al. |
| 5,376,254 A | 12/1994 | Fisher |
| 5,379,214 A | 1/1995 | Arbuckle et al. |
| 5,384,028 A | 1/1995 | Ito |
| 5,389,215 A | 2/1995 | Horiuchi et al. |
| 5,391,272 A | 2/1995 | O'Daly et al. |
| 5,393,903 A | 2/1995 | Gratzel et al. |
| 5,395,504 A | 3/1995 | Saurer et al. |
| 5,403,462 A | 4/1995 | Lev et al. |
| 5,405,511 A | 4/1995 | White et al. |
| 5,410,059 A | 4/1995 | Fraser et al. |
| 5,410,474 A | 4/1995 | Fox |
| 5,411,647 A | 5/1995 | Johnson et al. |
| 5,413,690 A | 5/1995 | Kost et al. |
| 5,413,764 A | 5/1995 | Haar |
| 5,418,142 A | 5/1995 | Kiser et al. |
| 5,421,189 A | 5/1995 | Dussault |
| 5,424,035 A | 5/1995 | Hones et al. |
| 5,426,032 A | 5/1995 | Phillips et al. |
| 5,427,912 A | 5/1995 | Brown et al. |
| 5,429,735 A | 7/1995 | Johnson et al. |
| 5,437,772 A | 8/1995 | DeCastro et al. |
| 5,437,999 A | 8/1995 | Diebold et al. |
| 5,438,271 A | 8/1995 | White et al. |
| 5,439,826 A | 8/1995 | Kontorovich |
| 5,445,967 A | 8/1995 | Deuter |
| 5,447,837 A | 9/1995 | Urnovitz |
| 5,449,898 A | 9/1995 | Dosmann |
| 5,453,360 A | 9/1995 | Yu |
| 5,468,366 A | 11/1995 | Wegner et al. |
| 5,469,846 A | 11/1995 | Khan |
| 5,470,533 A | 11/1995 | Shindo et al. |
| 5,477,326 A | 12/1995 | Dosmann |
| 5,489,414 A | 2/1996 | Schreiber et al. |
| 5,494,638 A | 2/1996 | Gullick |
| 5,500,350 A | 3/1996 | Baker et al. |
| 5,502,396 A | 3/1996 | Desarzens et al. |
| 5,504,011 A | 4/1996 | Gavin et al. |
| 5,508,171 A | 4/1996 | Walling et al. |
| 5,508,200 A | 4/1996 | Tiffany et al. |
| 5,508,203 A | 4/1996 | Fuller et al. |
| 5,509,410 A | 4/1996 | Hill et al. |
| 5,512,159 A | 4/1996 | Yoshioka et al. |
| 5,515,847 A | 5/1996 | Braig et al. |
| 5,518,689 A | 5/1996 | Dosmann et al. |
| 5,520,786 A | 5/1996 | Bloczynski et al. |
| 5,526,111 A | 5/1996 | Collins et al. |
| 5,526,120 A | 6/1996 | Jina et al. |
| 5,526,808 A | 6/1996 | Kaminsky et al. |
| 5,532,128 A | 7/1996 | Eggers et al. |
| 5,556,789 A | 8/1996 | Goerlach et al. |
| 5,552,116 A | 9/1996 | Yokota et al. |
| 5,554,531 A | 9/1996 | Zweig |
| 5,556,042 A | 10/1996 | Phillips et al. |
| 5,563,031 A | 10/1996 | Yu |
| 5,569,591 A | 10/1996 | Kell et al. |
| 5,569,608 A | 10/1996 | Sommer |
| 5,572,159 A | 11/1996 | McFarland |
| 5,575,403 A | 11/1996 | Charlton et al. |
| 5,575,895 A | 11/1996 | Ikeda et al. |
| 5,576,073 A | 11/1996 | Kickelhain |
| 5,580,794 A | 12/1996 | Allen |
| 5,589,045 A | 12/1996 | Hyodo |
| 5,589,326 A | 12/1996 | Deng et al. |
| 5,593,390 A | 1/1997 | Castellano et al. |
| 5,593,739 A | 1/1997 | Kickelhain |
| 5,594,906 A | 1/1997 | Holmes, II et al. |
| 5,597,532 A | 1/1997 | Connolly |
| 5,603,820 A | 2/1997 | Malinski et al. |

(56) References Cited

U.S. PATENT DOCUMENTS

| | | |
|---|---|---|
| 5,604,110 A | 2/1997 | Baker et al. |
| 5,605,662 A | 2/1997 | Heller et al. |
| 5,605,837 A | 2/1997 | Karimi et al. |
| 5,611,909 A | 3/1997 | Studer |
| 5,611,999 A | 3/1997 | Dosmann et al. |
| 5,620,579 A | 4/1997 | Genshaw et al. |
| 5,620,863 A | 4/1997 | Tomasco et al. |
| 5,620,890 A | 4/1997 | Kamps-Holtzapple et al. |
| 5,627,922 A | 5/1997 | Kopelman et al. |
| 5,628,890 A | 5/1997 | Carter et al. |
| 5,630,986 A | 5/1997 | Charlton et al. |
| 5,635,362 A | 6/1997 | Levine et al. |
| 5,635,364 A | 6/1997 | Clark et al. |
| 5,637,505 A | 6/1997 | Li et al. |
| 5,639,671 A | 6/1997 | Bogart et al. |
| 5,642,734 A | 7/1997 | Ruben et al. |
| 5,644,501 A | 7/1997 | Lin et al. |
| 5,645,798 A | 7/1997 | Schreiber et al. |
| 5,650,061 A | 7/1997 | Kuhr et al. |
| 5,650,062 A | 7/1997 | Ikeda et al. |
| 5,653,863 A | 8/1997 | Genshaw et al. |
| 5,654,178 A | 8/1997 | Fitzpatrick et al. |
| 5,656,502 A | 8/1997 | Mackay et al. |
| 5,658,443 A | 8/1997 | Yamamoto et al. |
| 5,658,802 A | 8/1997 | Hayes et al. |
| 5,660,791 A | 8/1997 | Brenneman et al. |
| 5,665,215 A | 9/1997 | Bussmann et al. |
| 5,670,031 A | 9/1997 | Hintsche et al. |
| 5,686,659 A | 11/1997 | Neel et al. |
| 5,691,486 A | 11/1997 | Behringer et al. |
| 5,691,633 A | 11/1997 | Liu et al. |
| 5,695,623 A | 12/1997 | Michel et al. |
| 5,698,083 A | 12/1997 | Glass |
| 5,700,695 A | 12/1997 | Yassinzadeh et al. |
| 5,701,181 A | 12/1997 | Boiarski et al. |
| 5,704,354 A | 1/1998 | Preidel et al. |
| 5,708,247 A | 1/1998 | McAleer et al. |
| 5,710,011 A | 1/1998 | Forrow et al. |
| 5,710,622 A | 1/1998 | Neel et al. |
| 5,719,667 A | 2/1998 | Miers |
| 5,720,862 A | 2/1998 | Hamamoto et al. |
| 5,723,284 A | 3/1998 | Ye |
| 5,723,345 A | 3/1998 | Yamauchi et al. |
| 5,727,548 A | 3/1998 | Hill et al. |
| 5,728,074 A | 3/1998 | Castellano et al. |
| 5,745,308 A | 4/1998 | Spangenberg et al. |
| 5,748,002 A | 5/1998 | Scott et al. |
| 5,757,666 A | 5/1998 | Schreiber et al. |
| 5,775,953 A | 5/1998 | Henning et al. |
| 5,759,364 A | 6/1998 | Charlton et al. |
| 5,759,794 A | 6/1998 | Levine et al. |
| 5,776,710 A | 7/1998 | Levine et al. |
| 5,780,304 A | 7/1998 | Matzinger et al. |
| 5,786,584 A | 7/1998 | Button et al. |
| 5,788,833 A | 8/1998 | Lewis et al. |
| 5,789,255 A | 8/1998 | Yu |
| 5,792,668 A | 8/1998 | Fuller et al. |
| 5,798,031 A | 8/1998 | Charlton et al. |
| 5,801,057 A | 9/1998 | Smart et al. |
| 5,807,375 A | 9/1998 | Gross et al. |
| 5,820,662 A | 10/1998 | Kubo et al. |
| 5,832,921 A | 11/1998 | Lennert et al. |
| 5,834,217 A | 11/1998 | Levine et al. |
| 5,837,546 A | 11/1998 | Allen et al. |
| 5,843,691 A | 12/1998 | Douglas et al. |
| 5,843,692 A | 12/1998 | Phillips et al. |
| 5,846,794 A | 12/1998 | Delobeau et al. |
| 5,849,174 A | 12/1998 | Sanghera et al. |
| 5,856,195 A | 1/1999 | Charlton et al. |
| 5,856,251 A | 1/1999 | Park et al. |
| 5,863,400 A | 1/1999 | Drummond et al. |
| 5,873,990 A | 2/1999 | Wojciechowski et al. |
| 5,874,046 A | 2/1999 | Megerle et al. |
| 5,883,378 A | 3/1999 | Irish et al. |
| 5,885,839 A | 3/1999 | Lingane et al. |
| 5,890,489 A | 4/1999 | Elden |
| 5,904,898 A | 5/1999 | Market |
| 5,911,872 A | 5/1999 | Lewis et al. |
| 5,916,156 A | 5/1999 | Hildenbrand et al. |
| 5,921,925 A | 7/1999 | Cartmell et al. |
| 5,922,530 A | 7/1999 | Yu |
| 5,922,591 A | 7/1999 | Anderson et al. |
| 5,925,021 A | 7/1999 | Castellano et al. |
| 5,942,102 A | 8/1999 | Hodges et al. |
| 5,945,341 A | 8/1999 | Howard, III |
| 5,948,289 A | 9/1999 | Noda et al. |
| 5,958,199 A | 9/1999 | Miyamto et al. |
| 5,965,380 A | 10/1999 | Heller et al. |
| 5,968,760 A | 10/1999 | Phillips et al. |
| 5,971,923 A | 10/1999 | Finger |
| 5,989,917 A | 11/1999 | McAleer et al. |
| 6,001,239 A | 12/1999 | Douglas et al. |
| 6,004,441 A | 12/1999 | Fujiwara et al. |
| 6,004,442 A | 12/1999 | Choulga et al. |
| 6,013,170 A | 1/2000 | Meade |
| 6,042,714 A | 3/2000 | Lin et al. |
| 6,044,285 A | 3/2000 | Chaiken et al. |
| 6,045,567 A | 4/2000 | Taylor et al. |
| 6,054,039 A | 4/2000 | Shieh |
| 6,061,128 A | 5/2000 | Zweig et al. |
| 6,069,011 A | 5/2000 | Riedel |
| 6,071,391 A | 6/2000 | Gotoh et al. |
| 6,087,182 A | 7/2000 | Jeng et al. |
| 6,091,975 A | 7/2000 | Daddona et al. |
| 6,102,872 A | 8/2000 | Doneen et al. |
| 6,103,033 A | 8/2000 | Say et al. |
| 6,103,509 A | 8/2000 | Sode |
| 6,110,354 A | 8/2000 | Saban et al. |
| 6,103,009 A | 9/2000 | Heller et al. |
| 6,120,676 A | 9/2000 | Heller et al. |
| 6,121,050 A | 9/2000 | Han |
| 6,124,461 A | 10/2000 | Say et al. |
| 6,126,609 A | 10/2000 | Keith et al. |
| 6,128,519 A | 10/2000 | Say |
| 6,129,823 A | 10/2000 | Hughes et al. |
| 6,136,549 A | 10/2000 | Feistel |
| 6,136,610 A | 10/2000 | Polito et al. |
| 6,143,164 A | 11/2000 | Heller et al. |
| 6,143,247 A | 11/2000 | Sheppard, Jr. et al. |
| 6,144,869 A | 11/2000 | Berner et al. |
| 6,150,124 A | 11/2000 | Riedel |
| 6,156,051 A | 12/2000 | Schraga |
| 6,156,173 A | 12/2000 | Gotoh et al. |
| 6,156,673 A | 12/2000 | Hintermaier et al. |
| 6,157,442 A | 12/2000 | Raskas |
| 6,157,472 A | 12/2000 | Eum et al. |
| 6,159,745 A | 12/2000 | Roberts et al. |
| 6,162,611 A | 12/2000 | Heller et al. |
| 6,162,639 A | 12/2000 | Douglas |
| 6,168,563 B1 | 1/2001 | Brown |
| 6,168,957 B1 | 1/2001 | Matzinger et al. |
| 6,170,318 B1 | 1/2001 | Lewis |
| 6,174,420 B1 | 1/2001 | Hodges et al. |
| 6,175,752 B1 | 1/2001 | Say et al. |
| 6,176,988 B1 | 1/2001 | Kessler |
| 6,179,979 B1 | 1/2001 | Hodges et al. |
| 6,180,062 B1 | 1/2001 | Naka et al. |
| 6,181,417 B1 | 1/2001 | Dosmann |
| 6,193,873 B1 | 2/2001 | Oharra et al. |
| 6,197,040 B1 | 3/2001 | LeVaughn et al. |
| 6,200,773 B1 | 3/2001 | Ouyang et al. |
| 6,201,607 B1 | 3/2001 | Roth et al. |
| 6,203,952 B1 | 3/2001 | O'Brian et al. |
| 6,206,282 B1 | 3/2001 | Hayes, Sr. et al. |
| 6,206,292 B1 | 3/2001 | Roberts et al. |
| 6,207,000 B1 | 3/2001 | Schwobel et al. |
| 6,212,417 B1 | 4/2001 | Ikeda et al. |
| 6,218,571 B1 | 4/2001 | Zhena et al. |
| 6,225,078 B1 | 5/2001 | Ikeda et al. |
| 6,226,081 B1 | 5/2001 | Fantone et al. |
| 6,233,471 B1 | 5/2001 | Berner et al. |
| 6,241,862 B1 | 5/2001 | McAleer et al. |
| 6,246,862 B1 | 5/2001 | Perry et al. |
| 6,246,966 B1 | 5/2001 | Perry |

(56) References Cited

U.S. PATENT DOCUMENTS

| | | |
|---|---|---|
| 6,251,260 B1 | 6/2001 | Heller et al. |
| 6,259,937 B1 | 7/2001 | Schulman et al. |
| 6,261,519 B1 | 7/2001 | Harding et al. |
| 6,262,749 B1 | 7/2001 | Finger et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,272,262 B1 | 8/2001 | Kopelman et al. |
| 6,272,364 B1 | 8/2001 | Kurnok |
| 6,275,717 B1 | 8/2001 | Gross et al. |
| 6,277,641 B1 | 8/2001 | Yager |
| 6,281,006 B1 | 8/2001 | Heller et al. |
| 6,284,550 B1 | 9/2001 | Carroll et al. |
| 6,287,595 B1 | 9/2001 | Loewy et al. |
| 6,294,281 B1 | 9/2001 | Heller |
| 6,294,787 B1 | 9/2001 | Schieferdecker et al. |
| 6,295,506 B1 | 9/2001 | Heinonen et al. |
| 6,299,757 B1 | 10/2001 | Feldman et al. |
| 6,300,142 B1 | 10/2001 | Vadgama et al. |
| 6,300,961 B1 | 10/2001 | Finger et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,326,160 B1 | 12/2001 | Dunn et al. |
| 6,329,161 B1 | 12/2001 | Heller et al. |
| 6,330,464 B1 | 12/2001 | Colvin, Jr. et al. |
| 6,335,203 B1 | 1/2002 | Patel et al. |
| 6,338,790 B1 | 1/2002 | Feldman et al. |
| 6,340,428 B1 | 1/2002 | Ikeada et al. |
| 6,342,364 B1 | 1/2002 | Watanabe et al. |
| 6,344,133 B1 | 2/2002 | Formica et al. |
| 6,349,230 B1 | 2/2002 | Kawanaka et al. |
| 6,358,752 B1 | 3/2002 | Durst et al. |
| 6,377,896 B1 | 4/2002 | Sato et al. |
| 6,379,513 B1 | 4/2002 | Chambers et al. |
| 6,379,915 B1 | 4/2002 | Douglas et al. |
| 6,339,258 B1 | 5/2002 | O'Brien et al. |
| 6,389,891 B1 | 5/2002 | D'Angelico et al. |
| 6,391,558 B1 | 5/2002 | Henkens et al. |
| 6,391,645 B1 | 5/2002 | Huang et al. |
| 6,394,952 B1 | 5/2002 | Anderson et al. |
| 6,395,227 B1 | 5/2002 | Kiser et al. |
| 6,401,532 B2 | 6/2002 | Lubbers |
| 6,413,398 B1 | 7/2002 | Geoff et al. |
| 6,414,213 B2 | 7/2002 | Ohmori et al. |
| 6,414,395 B1 | 7/2002 | Ookuma et al. |
| 6,414,410 B1 | 7/2002 | Nakamura et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,461,496 B1 | 10/2002 | Feldman et al. |
| 6,475,372 B1 | 11/2002 | Ohara et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,512,986 B1 | 1/2003 | Harmon |
| 6,514,718 B2 | 2/2003 | Heller et al. |
| 6,521,110 B1 | 2/2003 | Hodges et al. |
| 6,521,182 B1 | 2/2003 | Shade et al. |
| 6,525,330 B2 | 2/2003 | Paolini et al. |
| 6,525,549 B1 | 2/2003 | Poellmann |
| 6,526,298 B1 | 2/2003 | Khalil et al. |
| 6,531,040 B2 | 3/2003 | Musho et al. |
| 6,531,239 B2 | 3/2003 | Heller |
| 6,531,322 B1 | 3/2003 | Jurik et al. |
| 6,535,753 B1 | 3/2003 | Raskas |
| 6,537,498 B1 | 3/2003 | Lewis et al. |
| 6,538,735 B1 | 3/2003 | Duebendorfer et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas et al. |
| 6,549,796 B2 | 4/2003 | Sohrab |
| 6,551,494 B1 | 4/2003 | Heller et al. |
| 6,555,061 B1 | 4/2003 | Leong et al. |
| 6,558,528 B1 | 5/2003 | Matzinger |
| 6,558,529 B1 | 5/2003 | McVey et al. |
| 6,560,471 B1 | 5/2003 | Heller et al. |
| 6,562,625 B2 | 5/2003 | Modzelewski et al. |
| 6,565,509 B1 | 5/2003 | Say et al. |
| 6,570,390 B2 | 5/2003 | Hirayama et al. |
| 6,571,651 B1 | 5/2003 | Hodges |
| 6,572,822 B2 | 5/2003 | Jurki et al. |
| 6,574,425 B1 | 5/2003 | Weiss et al. |
| 6,576,416 B2 | 5/2003 | Haviland et al. |
| 6,576,461 B2 | 5/2003 | Heller et al. |
| 6,579,690 B1 | 5/2003 | Bonnecaze |
| 6,576,101 B1 | 6/2003 | Heller et al. |
| 6,591,125 B1 | 7/2003 | Buse et al. |
| 6,592,744 B1 | 7/2003 | Hodges et al. |
| 6,592,745 B1 | 7/2003 | Feldmen et al. |
| 6,594,514 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,618,934 B1 | 9/2003 | Feldmen et al. |
| 6,623,501 B2 | 9/2003 | Heller et al. |
| 6,627,057 B1 | 9/2003 | Bullar et al. |
| 6,632,349 B1 | 10/2003 | Hodges et al. |
| 6,636,652 B1 | 10/2003 | Kopelman et al. |
| 6,638,415 B1 | 10/2003 | Hodges et al. |
| 6,638,716 B2 | 10/2003 | Heller et al. |
| 6,645,359 B1 | 11/2003 | Bhullar et al. |
| 6,645,368 B1 | 11/2003 | Beaty et al. |
| 6,654,625 B1 | 11/2003 | Say et al. |
| 6,656,702 B1 | 12/2003 | Yugawa et al. |
| 6,656,741 B1 | 12/2003 | Nelson et al. |
| 6,676,816 B2 | 1/2004 | Mao et al. |
| 6,676,995 B2 | 1/2004 | Dick et al. |
| 6,689,265 B2 | 2/2004 | Heller et al. |
| 6,689,411 B2 | 2/2004 | Dick et al. |
| 6,690,836 B2 | 2/2004 | Natarajan et al. |
| 6,699,384 B1 | 3/2004 | Lin et al. |
| 6,749,740 B2 | 6/2004 | Liamos et al. |
| 6,790,341 B1 | 9/2004 | Saba et al. |
| 6,824,670 B2 | 11/2004 | Tokunaga et al. |
| 6,841,052 B2 | 1/2005 | Musho et al. |
| 6,890,421 B2 | 5/2005 | Oharra et al. |
| 6,893,545 B2 | 5/2005 | Gotoh et al. |
| 6,942,518 B2 | 9/2005 | Liamos et al. |
| 7,018,843 B2 | 3/2006 | Heller |
| 7,122,111 B2 | 10/2006 | Tokunaga et al. |
| 7,132,041 B2 | 11/2006 | Deng et al. |
| 7,176,146 B2 | 10/2007 | Wilsey |
| 7,351,323 B2 | 4/2008 | Iketaki et al. |
| 8,002,965 B2 | 8/2011 | Beer et al. |
| 8,026,104 B2 | 9/2011 | Wu et al. |
| 8,088,272 B2 | 1/2012 | Deng |
| 8,101,062 B2 | 1/2012 | Deng |
| 8,147,674 B2 | 4/2012 | Wu |
| 8,234,076 B2 | 7/2012 | Carpenter et al. |
| 8,262,899 B2 | 9/2012 | Wu |
| 8,287,717 B2 | 10/2012 | Wu |
| 8,337,691 B2 | 12/2012 | Lin et al. |
| 8,404,100 B2 | 3/2013 | Wu |
| 8,425,757 B2 | 4/2013 | Wu et al. |
| 8,470,604 B2 | 6/2013 | Wu et al. |
| 8,716,024 B2 | 5/2014 | Lin et al. |
| 8,871,517 B2 | 10/2014 | Lin et al. |
| 2001/0000129 A1 | 4/2001 | Raskas |
| 2001/0017269 A1 | 8/2001 | Heller et al. |
| 2001/0042683 A1 | 11/2001 | Musho et al. |
| 2002/0004106 A1 | 1/2002 | Leddy et al. |
| 2002/0012821 A1 | 1/2002 | Leddy et al. |
| 2002/0053523 A1 | 5/2002 | Liamos et al. |
| 2002/0079219 A1 | 6/2002 | Zhao et al. |
| 2002/0081588 A1 | 6/2002 | De Lumley-Woodyear et al. |
| 2002/0084196 A1 | 7/2002 | Liamos et al. |

(56) References Cited

U.S. PATENT DOCUMENTS

| | | |
|---|---|---|
| 2002/0125146 A1 | 9/2002 | Chan et al. |
| 2002/0139692 A1 | 10/2002 | Tokunaga et al. |
| 2002/0157967 A1 | 10/2002 | Ling et al. |
| 2002/0180446 A1 | 12/2002 | Kuhr et al. |
| 2003/0064525 A1 | 4/2003 | Liess |
| 2003/0148169 A1 | 4/2003 | Willmer et al. |
| 2003/0113933 A1 | 6/2003 | Rasmus et al. |
| 2003/0119208 A1 | 6/2003 | Yoon et al. |
| 2003/0136673 A1 | 7/2003 | Pilloud et al. |
| 2003/0146110 A1 | 8/2003 | Karinka et al. |
| 2003/0149348 A1 | 8/2003 | Raskas |
| 2003/0159927 A1 | 8/2003 | Lewis et al. |
| 2003/0175737 A1 | 9/2003 | Schulien et al. |
| 2003/0176183 A1 | 9/2003 | Drucker et al. |
| 2003/0178322 A1 | 9/2003 | Bolon et al. |
| 2003/0199744 A1 | 10/2003 | Buse et al. |
| 2003/0201194 A1 | 10/2003 | Heller et al. |
| 2003/0205465 A1 | 11/2003 | Feng et al. |
| 2003/0209450 A1 | 11/2003 | McVey et al. |
| 2004/0005716 A9 | 1/2004 | Beaty et al. |
| 2004/0007461 A1 | 1/2004 | Edelbrock |
| 2004/0026253 A1 | 2/2004 | Leddy et al. |
| 2004/0029946 A1 | 2/2004 | Arora et al. |
| 2004/0033165 A1 | 2/2004 | Lewis et al. |
| 2004/0040840 A1 | 3/2004 | Mao et al. |
| 2004/0045821 A1 | 3/2004 | Cui et al. |
| 2004/0054267 A1 | 3/2004 | Feldmen et al. |
| 2004/0055898 A1 | 3/2004 | Heller et al. |
| 2004/0060818 A1 | 4/2004 | Feldmen et al. |
| 2004/0061841 A1 | 4/2004 | Black et al. |
| 2004/0074472 A1 | 4/2004 | Kumar et al. |
| 2004/0079653 A1 | 4/2004 | Karinka et al. |
| 2004/0099531 A1 | 5/2004 | Srinivasan et al. |
| 2004/0118682 A1 | 6/2004 | Murray et al. |
| 2004/0149577 A1 | 8/2004 | Kumar et al. |
| 2004/0157337 A1 | 8/2004 | Burke et al. |
| 2004/0157338 A1 | 8/2004 | Burke et al. |
| 2004/0157339 A1 | 8/2004 | Burke et al. |
| 2004/0180444 A1 | 9/2004 | Rannikko et al. |
| 2004/0224137 A1 | 11/2004 | Rogalska et al. |
| 2004/0225230 A1 | 11/2004 | Liamos et al. |
| 2004/0256248 A1 | 12/2004 | Burke et al. |
| 2004/0259180 A1 | 12/2004 | Burke et al. |
| 2004/0260511 A1 | 12/2004 | Burke et al. |
| 2005/0009126 A1 | 1/2005 | Andrews et al. |
| 2005/0049473 A1 | 3/2005 | Desai et al. |
| 2005/0069892 A1 | 3/2005 | Lyengar et al. |
| 2005/0164322 A1 | 7/2005 | Heller et al. |
| 2005/0176153 A1 | 8/2005 | O'hara et al. |
| 2005/0247562 A1 | 11/2005 | Tokunaga et al. |
| 2006/0063218 A1 | 3/2006 | Bartkowiak et al. |
| 2006/0074564 A1 | 4/2006 | Bartkowiak et al. |
| 2006/0085137 A1 | 4/2006 | Bartkowiak et al. |
| 2006/0191787 A1 | 8/2006 | Wang et al. |
| 2007/0074977 A1 | 4/2007 | Guo et al. |
| 2007/0080073 A1 | 4/2007 | Wu et al. |
| 2007/0256943 A1 | 11/2007 | Popovich et al. |
| 2008/0102441 A1 | 5/2008 | Chen et al. |
| 2008/0145878 A1 | 6/2008 | Marfurt |
| 2008/0149480 A1 | 6/2008 | Bell |
| 2008/0311613 A1 | 12/2008 | Stefaniak et al. |
| 2009/0014339 A1 | 1/2009 | Beer et al. |
| 2009/0026094 A1 | 1/2009 | Deng et al. |
| 2009/0084687 A1* | 4/2009 | Chatelier ............... C12Q 1/001 205/792 |
| 2009/0305317 A1 | 12/2009 | Brauer et al. |
| 2012/0211361 A1 | 8/2012 | Wu |
| 2012/0298507 A1 | 11/2012 | Wu |
| 2013/0240377 A1 | 9/2013 | Wu |
| 2014/0174951 A1 | 6/2014 | Beer et al. |

FOREIGN PATENT DOCUMENTS

| | | |
|---|---|---|
| CN | 1322299 | 10/2000 |
| CN | 1328156 | 12/2001 |
| CN | 1598564 | 10/2004 |
| DE | 229500 | 6/1985 |
| DE | 271179 | 8/1989 |
| DE | 4003194 | 8/1991 |
| DE | 4100727 | 7/1992 |
| DE | 19944318891 | 12/1994 |
| DE | 19824629 | 12/1999 |
| DE | 69915850 | 1/2005 |
| EP | 34049 | 8/1981 |
| EP | 57110 | 8/1982 |
| EP | 120715 | 10/1984 |
| EP | 121385 | 10/1984 |
| EP | 127958 | 12/1984 |
| EP | 10375 | 12/1985 |
| EP | 164180 | 12/1985 |
| EP | 255291 | 2/1986 |
| EP | 206218 | 12/1986 |
| EP | 213343 | 3/1987 |
| EP | 215678 | 3/1987 |
| EP | 230472 | 8/1987 |
| EP | 241309 | 10/1987 |
| EP | 287883 | 10/1988 |
| EP | 330517 | 2/1989 |
| EP | 354441 | 2/1990 |
| EP | 359531 | 3/1990 |
| EP | 359831 | 3/1990 |
| EP | 383322 | 8/1990 |
| EP | 417796 | 3/1991 |
| EP | 470649 | 2/1992 |
| EP | 471986 | 2/1992 |
| EP | 537761 | 4/1993 |
| EP | 546536 | 6/1993 |
| EP | 546796 | 6/1993 |
| EP | 0628810 | 12/1994 |
| EP | 636880 | 2/1995 |
| EP | 640832 | 3/1995 |
| EP | 651250 | 5/1995 |
| EP | 186286 | 7/1996 |
| EP | 732406 | 9/1996 |
| EP | 732590 | 9/1996 |
| EP | 0741186 | 11/1996 |
| EP | 0762112 | 3/1997 |
| EP | 800086 | 10/1997 |
| EP | 837320 | 4/1998 |
| EP | 840122 | 5/1998 |
| EP | 851224 | 7/1998 |
| EP | 859230 | 8/1998 |
| EP | 878708 | 11/1998 |
| EP | 878713 | 11/1998 |
| EP | 887421 | 12/1998 |
| EP | 894509 | 2/1999 |
| EP | 942278 | 9/1999 |
| EP | 964059 | 12/1999 |
| EP | 1156324 | 11/2002 |
| EP | 1279742 | 1/2003 |
| EP | 1411348 | 4/2004 |
| EP | 1 557 662 | 7/2005 |
| EP | 1 840 219 | 10/2007 |
| ES | 2184236 | 1/2003 |
| ES | 2223185 | 2/2005 |
| FR | 2325920 | 9/1976 |
| GB | 2295676 | 6/1996 |
| JP | 62209350 | 9/1987 |
| JP | 3260739 | 11/1991 |
| JP | 09089832 | 4/1997 |
| JP | 11087213 | 3/1999 |
| JP | 2120657 | 5/1999 |
| JP | 2003028826 | 1/2003 |
| JP | 200361650 | 3/2003 |
| JP | 200403478 | 1/2004 |
| JP | 2004093478 | 3/2004 |
| JP | 2004300328 | 10/2004 |
| JP | 2005147990 | 6/2005 |
| WO | WO 1981/001794 | 7/1981 |
| WO | WO 1982/003729 | 10/1982 |

(56) References Cited

FOREIGN PATENT DOCUMENTS

| | | |
|---|---|---|
| WO | WO 1983/000926 | 3/1983 |
| WO | WO 1986/000138 | 1/1986 |
| WO | WO 1986/002732 | 5/1986 |
| WO | WO 1990/005293 | 5/1990 |
| WO | WO 1990/005910 | 5/1990 |
| WO | WO 1992/001928 | 2/1992 |
| WO | WO 1992/007655 | 5/1992 |
| WO | WO 1992/015704 | 9/1992 |
| WO | WO 1992/015859 | 9/1992 |
| WO | WO 1992/015861 | 9/1992 |
| WO | WO 1992/015950 | 9/1992 |
| WO | WO 1992/019961 | 11/1992 |
| WO | WO 1992/022669 | 12/1992 |
| WO | WO 1993/009433 | 5/1993 |
| WO | WO 1993/21928 | 11/1993 |
| WO | WO 1995/03542 | 2/1995 |
| WO | WO 1995/007050 | 3/1995 |
| WO | WO 1995/13535 | 5/1995 |
| WO | WO 1995/13536 | 5/1995 |
| WO | WO 1995/022597 | 8/1995 |
| WO | WO 1996/004398 | 2/1996 |
| WO | WO 1996/007908 | 3/1996 |
| WO | WO 1996/013707 | 5/1996 |
| WO | WO 1996/015454 | 5/1996 |
| WO | WO 1996/014026 | 10/1996 |
| WO | WO 1996/033403 | 10/1996 |
| WO | WO 1997/000441 | 1/1997 |
| WO | WO 1997/002487 | 1/1997 |
| WO | WO 1997/008544 | 3/1997 |
| WO | WO 1997/016726 | 5/1997 |
| WO | WO 1997/018465 | 5/1997 |
| WO | WO 1997/029366 | 8/1997 |
| WO | WO 1997/029847 | 8/1997 |
| WO | WO 1997/030344 | 8/1997 |
| WO | WO 1997/039343 | 10/1997 |
| WO | WO 1997/042882 | 11/1997 |
| WO | WO 1997/042888 | 11/1997 |
| WO | WO 1997/045719 | 12/1997 |
| WO | WO 1998/005424 | 2/1998 |
| WO | WO 1998/019153 | 5/1998 |
| WO | WO 1998/019159 | 5/1998 |
| WO | WO 1998/029740 | 7/1998 |
| WO | WO 1998/044342 | 10/1998 |
| WO | WO 1998/058246 | 12/1998 |
| WO | WO 1998/058250 | 12/1998 |
| WO | WO 1999/022227 | 5/1999 |
| WO | WO 1999/22230 | 5/1999 |
| WO | WO 1999/045375 | 9/1999 |
| WO | WO 1999/67628 | 12/1999 |
| WO | WO 2000/016089 | 3/2000 |
| WO | WO 2000/020626 | 4/2000 |
| WO | WO 2000/020855 | 4/2000 |
| WO | WO 2000/029540 | 5/2000 |
| WO | WO 2000/057011 | 9/2000 |
| WO | WO 2000/077523 | 12/2000 |
| WO | WO 2001/003207 | 1/2001 |
| WO | WO 2001/033206 | 5/2001 |
| WO | WO 2001/33216 | 5/2001 |
| WO | WO 2001/056771 | 8/2001 |
| WO | WO 2001/057510 | 8/2001 |
| WO | WO 2001/057513 | 8/2001 |
| WO | WO 2001/65246 | 9/2001 |
| WO | WO 2001/67099 | 9/2001 |
| WO | WO 2002/001214 | 1/2002 |
| WO | WO 2002/031482 | 4/2002 |
| WO | WO 2002/031481 | 10/2002 |
| WO | WO 2002/077633 | 10/2002 |
| WO | WO 2003/001195 | 1/2003 |
| WO | WO 2003/069304 | 2/2003 |
| WO | WO 2003/066554 | 6/2003 |
| WO | WO 2003/087802 | 10/2003 |
| WO | WO 2004/023128 | 3/2004 |
| WO | WO 2004/040286 | 5/2004 |
| WO | WO 2004/046707 | 6/2004 |
| WO | WO 2004/053476 | 6/2004 |
| WO | WO 2004/062801 | 7/2004 |
| WO | WO 2004/113896 | 12/2004 |
| WO | WO 2004/113912 | 12/2004 |
| WO | WO 2004/113913 | 12/2004 |
| WO | WO 2005/001462 | 1/2005 |
| WO | WO 2005/001463 | 1/2005 |
| WO | WO 2005/003622 | 1/2005 |
| WO | WO 2005/003748 | 1/2005 |
| WO | WO 2005/008231 | 1/2005 |
| WO | WO 2005/022143 | 3/2005 |
| WO | WO 2005/040407 | 5/2005 |
| WO | WO 2005/045234 | 5/2005 |
| WO | WO 2005/078118 | 8/2005 |
| WO | WO 2006/012940 | 2/2006 |
| WO | WO 2006/079797 | 8/2006 |
| WO | WO 2006/110504 | 10/2006 |

OTHER PUBLICATIONS

Hall, J.W. et al., "Automated Determination of Glucose using ENZ Glucose Oxidase and Potassium Ferrocyanide ENZ Peroxidase," Analytical Biochemistry, vol. 26, No. 1, 1968, pp. 12-17.

Stanislawski et al., "Immunotoxins Containing Glucose Oxidase and Lactoperoxidase With Tumoricidal Properties: In-Vitro Killing Effectiveness in a Mouse Plasmacytoma Cell Model," Cancer Research 49, pp. 5497-5504 (Oct. 15, 1989).

Yao, et al., "A Thin-Film Glucose Electrode System with Compensation for Drifit", 1989, pp. 742-744, vol. XX XV.

Yao, et al., "The Low-Potential Approach of Glucose Sensing", 1986, pp. 139-146, vol. BME-33, No. 2.

PCT Search Report for International Application No. PCT/US2008/085903 dated May 18, 2009 (6 pages).

PCT Written Opinion for International Application No. PCT/US2008/085903 dated May 18, 2009 (11 pages).

* cited by examiner

METHOD OF USING AN ELECTROCHEMICAL TEST SENSOR

CROSS REFERENCE TO RELATED APPLICATIONS

This application is a divisional of U.S. application Ser. No. 14/105,839 filed Dec. 13, 2013; U.S. application Ser. No. 14/105,839 is a continuation of U.S. application Ser. No. 13/682,380 filed Nov. 20, 2012; U.S. application Ser. No. 13/682,380 is a divisional of U.S. application Ser. No. 12/316,133 filed Dec. 10, 2008, which issued as U.S. Pat. No. 8,337,691 B2 on Dec. 25, 2012, all of which claim priority to U.S. Provisional Application No. 61/007,211, filed Dec. 10, 2007, the contents of which are incorporated entirely herein by reference.

FIELD OF THE INVENTION

The present invention generally relates to a method of using an electrochemical test sensor. More specifically, the present invention generally relates to using control markers for auto-detection of the control solution in electrochemical test sensors.

BACKGROUND OF THE INVENTION

The quantitative determination of analytes in body fluids is of great importance in the diagnoses and maintenance of certain physical conditions. For example, lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

The test sensor is adapted to receive fluid (e.g., blood) from a user. The test sensor typically includes a base and a lid that is attached to the base. One type of test sensor is an electrochemical test sensor that is adapted to test for an analyte (e.g., glucose). Electrochemical test sensors typically include at least two electrodes to analyze the analyte concentration of the sample. These electrodes of the test sensor are in electrical communication with a meter or instrument that is configured to test for the analyte concentration.

A potential is applied to the electrodes in contact with a biological sample and reagents. The resulting current is measured while the analyte is reacting with the reagents, and then correlated with the amount of an analyte in the sample. Such instruments are referred to as amperometric, in contrast with coulometric instruments that measure the total charge in coulombs produced from reaction of the sample by integrating the current over the entire measurement time. The amperometric instruments are advantageous in that they can use smaller samples and perform quicker tests. Specifically, amperometric instruments do not need to wait for the entire volume of the analyte to be reacted, but rather may take measurements of the analyte by sampling the reaction rate at a predetermined time.

To obtain more accurate measurements, control solutions containing known amounts of glucose are used to verify that the instrument is operating properly. Control solutions have been used that contain blood serum. Some control solutions have been used that replace serum-based control solutions with solutions free of serum, since serum-free solutions are more consistent and stable than those containing serum. Control solutions may contain multiple fixed levels of an analyte concentration (e.g., two or three fixed glucose concentrations) that are formulated to mimic blood serum in terms of fluidity.

Control solutions are used to check the functionality of the analyte monitoring device or meter. Control solutions need to be identified and separated from the readings of real whole blood samples. Specifically, there is a need to automatically detect the control solution by the meter for several reasons. First, the temperature coefficients of the control solution and whole blood may be different. Thus, it is desirable to compensate the temperature effect on glucose readings with separate temperature coefficients. Second, by automatically detecting the control solution and not recording its reading into the memory of real blood-glucose readings assists to provide a more accurate average of blood-glucose readings. Without eliminating the control-solution readings, control solutions will be included in the history of the glucose measurements. Having incorrect historical readings may lead to an incorrect interpretation of a patient's diabetic condition. Additionally, if a control solution is substituted for a whole blood sample, it may be erroneously considered by a physician as indicating a need to change treatment. Third, automatically detecting the control solution and not recording its reading into the memory of blood-glucose readings may minimize the chance of faking the blood-glucose readings by control solution.

Therefore, it would be desirable to have an improved control marker for auto-detection of the control solution and method of using the same.

SUMMARY OF THE INVENTION

According to one method, a control solution is distinguished from a sample during operation of an electrochemical test sensor measuring the amount of an analyte in the control solution and in the sample. A control marker is added to the control solution. The control marker is adapted to be electrochemically oxidized at a potential higher than the potential needed to measure the oxidation of the analyte. The control marker includes sodium iodide, triethanolamine, tripropanolamine, tributanolamine, 2,5-dihydroxybenzoic acid, xylenol orange, hydroquinone sulfonic acid, cresol red, 3-[4-(hydroxyphenyl)amino]-3-oxopropanoic acid, N-acetyl-5-aminosalicyclic acid, N-ethyl-N-(3-sulfopropyl)-3-methylaniline (TOPS), 3-(N-ethyl-3-methylanilino)-2-hydroxypropanesulfonic acid (TOOS), 8-anilino-1-naphthalenesulfonic acid, 8-anilino-1-naphthalenesulfonic acid, 2-napthylamine 1-sulfonic acid, sodium diphenylamine-4-sulfonate, N-ethyl-N-(2-hydroxy-3-sulfopropyl)-3,5-dimethylaniline (MAOS), or salts thereof. The control solution, the control marker and a predetermined amount of the analyte is introduced to the electrochemical test sensor. The test sensor includes a working electrode, a counter electrode and a reagent. A potential is applied at least once to the test sensor sufficient to oxidize the control marker and the analyte. The resulting electrical current is measured. A potential is applied at least once to the electrochemical test sensor in which the potential is sufficient to measure oxidation of the analyte and not sufficient to oxidize the control marker. The resulting electrical current is measured. Determining whether a control solution or a sample is present based on the measured electrical currents is then performed.

According to one embodiment, a control solution for use in testing an electrochemical system for measuring the amount of an analyte in a sample includes a predetermined amount of the analyte and a predetermined amount of a control marker. The control marker is adapted to be oxidized at a potential higher than the potential required to oxidize the analyte. The control marker includes sodium iodide, triethanolamine, tripropanolamine, tributanolamine, 2,5-dihydroxybenzoic acid, xylenol orange, hydroquinone sulfonic acid, cresol red, 3-[4-(hydroxyphenyl)amino]-3-oxopropanoic acid, N-acetyl-5-aminosalicyclic acid, N-ethyl-N-(3-sulfopropyl)-3-methylaniline (TOPS), 3-(N-ethyl-3-methylanilino)-2-hydroxypropanesulfonic acid (TOOS), 8-anilino-1-naphthalenesulfonic acid, 8-anilino-1-naphthalenesulfonic acid, 2-napthylamine 1-sulfonic acid, sodium diphenylamine-4-sulfonate, N-ethyl-N-(2-hydroxy-3-sulfopropyl)-3,5-dimethylaniline (MAOS), or salts thereof. The predetermined amount of the control marker is proportional to the predetermined amount of analyte such that the presence of the control marker is detectable.

According to another method, a control solution is distinguished from a sample during operation of an electrochemical test sensor in which the electrochemical test sensor measuring the information related to an analyte. A control solution is provided including a control marker and a predetermined amount of analyte. The control marker has a higher potential than the potential needed to measure the oxidation of the analyte. The control marker includes sodium iodide, triethanolamine, tripropanolamine, tributanolamine, 2,5-dihydroxybenzoic acid, xylenol orange, hydroquinone sulfonic acid, cresol red, 3-[4-(hydroxyphenyl)amino]-3-oxopropanoic acid, N-acetyl-5-aminosalicyclic acid, N-ethyl-N-(3-sulfopropyl)-3-methylaniline (TOPS), 3-(N-ethyl-3-methylanilino)-2-hydroxypropanesulfonic acid (TOOS), 8-anilino-1-naphthalenesulfonic acid, 8-anilino-1-naphthalenesulfonic acid, 2-napthylamine 1-sulfonic acid, sodium diphenylamine-4-sulfonate, N-ethyl-N-(2-hydroxy-3-sulfopropyl)-3,5-dimethylaniline (MAOS), or salts thereof. An electrochemical sensor having a working electrode, a counter electrode and a reagent is provided. The control solution is introduced to the electrochemical test sensor. A potential is applied to the electrochemical test sensor sufficient to oxidize the control marker and the analyte. The resulting electrical current is measured. A lower potential is applied to the electrochemical test sensor in which the lower potential is sufficient to oxidize the analyte and not sufficient to oxidize the control marker. The resulting electrical current is measured. Determining whether a control solution or a sample is present based on the measured electrical currents is then performed.

According to a further method, a control solution is distinguished from a sample during operation of an electrochemical test sensor measuring the amount of an analyte in the control solution and in the sample. A control marker is added to the control solution. The control marker is adapted to be electrochemically oxidized at a potential higher than the potential needed to measure the oxidation of the analyte. The control solution, the control marker and a predetermined amount of the analyte are introduced to the electrochemical test sensor. The test sensor includes a working electrode, a counter electrode and a reagent. The control solution includes a sufficient amount of anionic polymer to increase the electrical current by at least 5% as compared to a control solution in the absence of an anionic polymer. A potential is applied at least once to the test sensor sufficient to oxidize the control marker and the analyte. The resulting electrical current is measured. A potential is applied at least once to the electrochemical test sensor lower than the previous potential. The potential is sufficient to measure oxidation of the analyte and not sufficient to oxidize the control marker. The resulting electrical current is measured. Determining whether a control solution or a sample is present based on the measured electrical currents.

According to yet another method, a control solution is distinguished from a sample during operation of an electrochemical test sensor measuring the amount of an analyte in the control solution and in the sample. The control marker is then added to the control solution. The control marker is adapted to be electrochemically oxidized at a potential higher than the potential needed to measure the oxidation of the analyte. The control solution, the control marker and a predetermined amount of the analyte are introduced to the electrochemical test sensor. The test sensor includes a working electrode, a counter electrode and a reagent. The control solution includes a sufficient amount of salt to increase the electrical current by at least 5% as compared to a control solution in the absence of a salt to increase the measured current. A potential is applied at least once to the test sensor sufficient to oxidize the control marker and the analyte. The resulting electrical current is measured. A potential is applied at least once to the electrochemical test sensor lower than the previous potential. The potential is sufficient to measure oxidation of the analyte and not sufficient to oxidize the control marker. The resulting electrical current is measured. Determining whether a control solution or a sample is present based on the measured electrical currents is then performed.

According to another method, the concentration of an analyte in a fluid sample is determined. The fluid sample is introduced to a test sensor. At least transferring one electron from the analyte in the sample to a mediator in the test sensor. A pulse sequence is applied to the sample. The pulse sequence includes at least two duty cycles within 180 seconds. At least one of the duty cycles having a first potential in a first excitation period and a first relaxation period. After one of the duty cycles, providing a second potential to the sample. The second potential is greater than the first potential. The second potential is supplied after a second relaxation period. The second relaxation period is less than the first relaxation period. Analyzing a current responsive to the excitation of the measurable species. Determining whether a control solution or a sample is present based on the measured electrical currents is then performed.

DETAILED DESCRIPTION OF ILLUSTRATED EMBODIMENTS

The present invention is directed to a control marker (also referred to as an internal reference) and a method of using the same. A control marker is an additive to a liquid control solution. The control marker is configured to generate a distinctive current profile using a detection algorithm. By having a distinctive current profile, the meter or instrument can automatically distinguish a control test from an analyte-fluid test (e.g., a glucose blood sample).

The control marker is used in an electrochemical test sensor that is adapted to assist in determining information related to an analyte, such as an analyte concentration. The electrochemical test sensors are adapted to receive a fluid sample and be analyzed using an instrument or meter. The electrochemical test sensor assists in determining information related to the analytes such as analyte concentrations. Analytes that may be measured include glucose, cholesterol, lipid profiles, microalbumin, urea, creatinine, creatine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

Figure 1A:
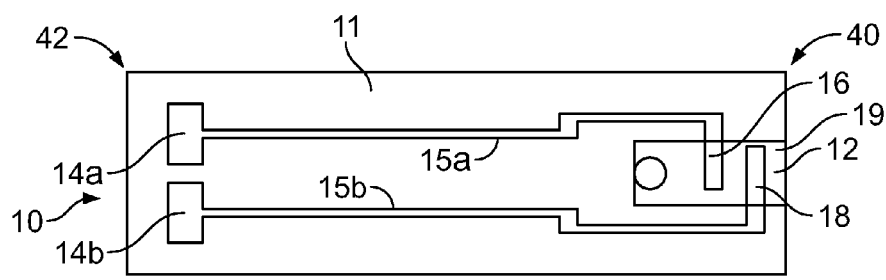
FIG. 1A is a test sensor according to one embodiment.

The test sensors described herein are electrochemical test sensors. Meters used with the electrochemical test sensors may have optical aspects so as to detect the calibration information and electrochemical aspects to determine the information related to the analyte (e.g., analyte concentration of the fluid sample). One non-limiting example of an electrochemical test sensor is shown in FIG. 1A. FIG. 1A depicts a test sensor 10 including a base 11, a capillary channel, and a plurality of electrodes 16 and 18. A region 12 shows an area that defines the capillary channel (e.g., after a lid is placed over the base 11). The plurality of electrodes includes a counter electrode 16 and a working (measuring) electrode 18. The electrochemical test sensor may also contain at least three electrodes, such as a working electrode, a counter electrode, a trigger electrode, or a hematocrit electrode. The working electrode employed in electrochemical test sensors according to the embodiments of the present invention may vary, with suitable electrodes including, but not limited to, carbon, platinum, palladium, gold, ruthenium, rhodium and combinations thereof.

The electrodes 16, 18 are coupled to a plurality of conductive leads or traces 15a,b, which, in the illustrated embodiment, terminates with larger areas designated as test-sensor contacts 14a,b. The capillary channel is generally located in a fluid-receiving area 19. It is contemplated that other electrochemical test sensors may be used with the control markers discussed in the present invention.

The fluid-receiving area 19 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically includes an analyte-specific enzyme that reacts with the analyte and with an electron acceptor to produce an electrochemically measurable species that may be detected by the electrodes. Enzymes that may be used with glucose include glucose oxidase and glucose dehydrogenase. If information of another analyte is desired, an appropriate enzyme is selected to react with the analyte. One non-limiting example in detecting glucose includes using an enzyme of glucose oxidase, a mediator of a ferricyanide salt and buffer to maintain a pH of from about 5 to about 7. Another non-limiting example in detecting glucose includes using an enzyme of glucose dehydrogenase, a co-factor such as pyrroloquinoline quinone (PQQ), and a buffer to maintain a pH of from about 6 to about 8.

The reagent typically includes a mediator that assists in transferring electrons between the analyte and the electrodes. The reagent may include binders that hold the enzyme and mediator together, other inert ingredients, buffers or combinations thereof.

A fluid sample (e.g., blood) may be applied to the fluid-receiving area 19. The fluid sample reacts with the at least one reagent. After reacting with the reagent and in conjunction with the plurality of electrodes, the fluid sample produces electrical signals that assist in determining the analyte concentration. The conductive leads 15a,b carry the electrical signal back toward a second opposing end 42 of the test sensor 10 where the test-sensor contacts 14a,b transfer the electrical signals into the meter.

Figure 1B:
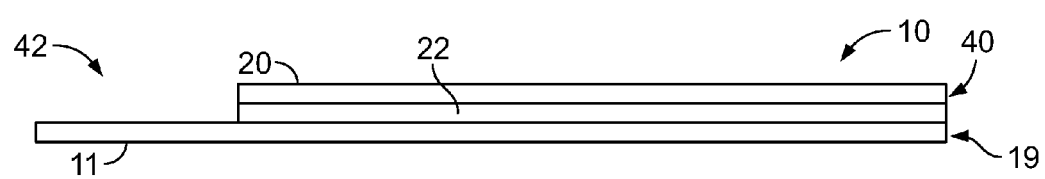
FIG. 1B is a side view of the test sensor of FIG. 1A.

Referring to FIG. 1B, a side view of the test sensor 10 of FIG. 1A is shown. As shown in FIG. 1B, the test sensor 10 of FIG. 1B further includes a lid 20 and a spacer 22. The base 11, the lid 20, and the spacer 22 may be made from a variety of materials such as polymeric materials. Non-limiting examples of polymeric materials that may be used to form the base 11, the lid 20, and the spacer 22 include polycarbonate, polyethylene terephthalate (PET), polyethylene naphthalate (PEN), polyimide, and combinations thereof. It is contemplated that other materials may be used in forming the base 11, lid 20, and/or spacer 22.

To form the test sensor 10 of FIGS. 1A, 1B, the base 11, the spacer 22, and the lid 20 are attached by, for example, an adhesive or heat sealing. When the base 11, the lid 20, and the spacer 22 are attached, the fluid-receiving area 19 is formed. The fluid-receiving area 19 provides a flow path for introducing the fluid sample into the test sensor 10. The fluid-receiving area 19 is formed at a first end or testing end 40 of the test sensor 10. Test sensors of the embodiments of the present invention may be formed with a base and a lid in the absence of a spacer, where the fluid-receiving area is formed directly in the base and/or the lid.

It is also contemplated that the electrochemical test sensor may be formed in the absence of a spacer. For example, the electrochemical test sensor may include a base and a lid such that a channel (e.g., capillary channel) is formed when the base and the lid are attached to each other.

The base, spacer and lid may be made from a variety of materials such as polymeric materials. Non-limiting examples of polymeric materials that may be used to form the base, spacer and lid include polycarbonate, polyethylene terephthalate (PET), polystyrene, polyimide, and combinations thereof. It is contemplated that the base, spacer and lid may be independently made of other materials. Depending on the selected control solutions, the electrode pattern may be made from a variety of conductive materials including, but not limited to, gold, platinum, rhodium, palladium, ruthenium, carbon or combinations thereof. Carbon electrodes may be desirable depending on the selected control solution.

In one method, an electrochemical test sensor for measuring an analyte in a fluid (e.g., glucose in a whole blood sample), the working and counter electrodes are coated with reagent by, for example, co-printing or co-depositing. The reagent typically includes some polymers and the reactive ingredients. Some reactive ingredients include an enzyme that oxidizes the analyte (e.g., glucose) in the fluid sample and a mediator, which is a redox compound that re-oxidizes the enzyme after it has been reduced by oxidizing analyte. The reduced mediator carries electrons from the enzymatic reaction of glucose oxidation to the working electrode and is re-oxidized at the electrode surface. The applied voltage differential between the two electrodes results in the mediator passing electrons to the working electrode, creating a measurable current that is proportional to the amount of glucose in the sample. The test sensor also may comprise single or multiple reagent layers, or may comprise different single or multiple reagent layers at each electrode, working and counter electrodes.

Figure 2:
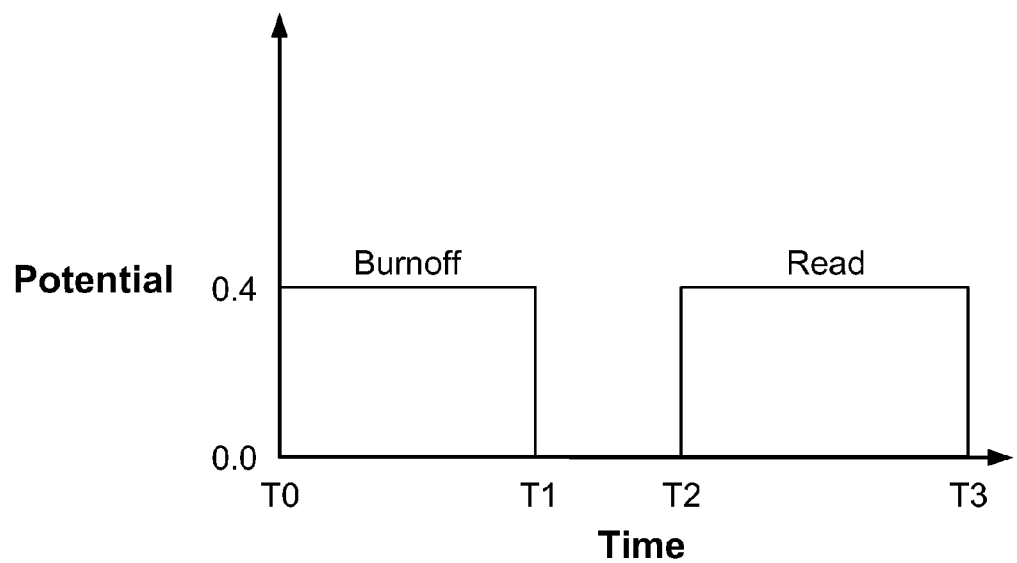
FIG. 2 is one plot of potential versus time for a burn period.
Figure 3:
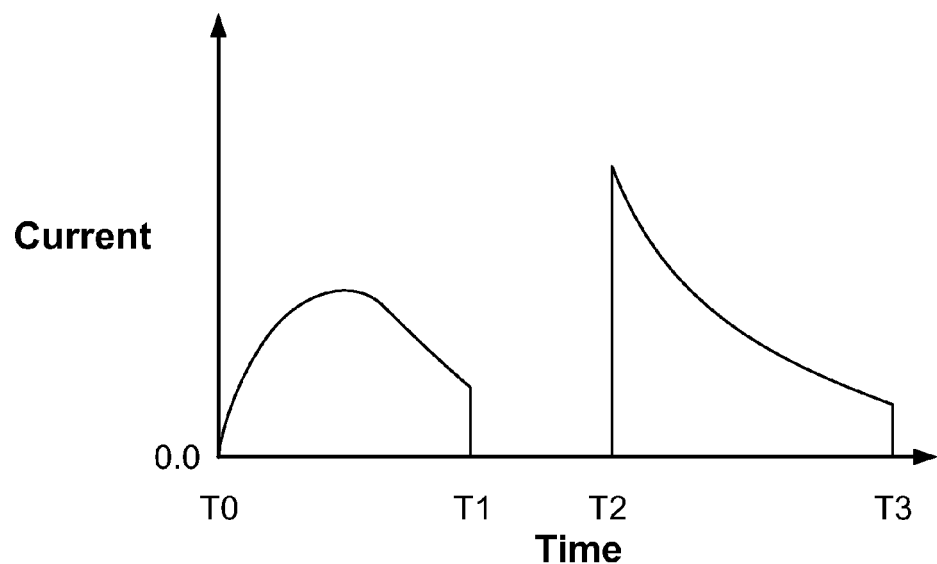
FIG. 3 is one plot of current versus time for the potential applied as FIG. 2.

Electrochemical test sensors and, more specifically, amperometric test sensors apply a fixed potential across the electrodes and the current produced is measured over a predetermined period of time (e.g., 5 or 10 seconds) to correct for the bias that may be present due to premature reduction of the mediator. In one system, a potential is applied for two periods of time, separated by a resting period. A typical plot of the potential versus time for the first or "burn period" is presented in FIG. 2. FIG. 3 shows a typical plot of current versus time. The current rises to a peak while the sample is rehydrating the reagent layer, enabling the oxidation and reduction reactions to occur and then declines as diffusion begins to control. After this brief period, the applied potential is removed or at least reduced during a resting period, while the oxidation of glucose and reduction of the mediator continue. Then, the potential is reapplied for a second period and the current measured over the "read" period (e.g., 10 seconds). Since reduced mediator is present as the result of the concomitant oxidation of the enzyme, the current produced initially is high, but then it declines rapidly and approaches a steady state diffusion-controlled condition. The current recorded at the end of the short "read" period is used to determine the glucose content of the blood sample, through a previously obtained correlation between the current at the end of the read period and the glucose contained in test samples having known concentrations.

As discussed above, it is highly desirable for the control solution to provide accurate analyte readings and be distinguishable from a biological sample. The present invention employs an oxidizable species (i.e., a control marker) that is oxidizable only at voltages higher than those used for the analyte (e.g., glucose) measurements. This means that at a low potential adequate to fully oxidize the analyte-related mediator, but not the control marker, only the analyte will be measured. The term control marker is also referred to as an internal reference. When the potential is high enough to oxidize the added control marker, both the analyte and the control marker will be oxidized. Although the analyte (e.g., glucose) is oxidized at the higher potential, the measurement made at a lower voltage is already diffusion-limited and does not depend on the total amount of analyte oxidized by the enzyme. It is feasible, therefore, to add such control markers to a control solution and to use it to identify the solution as a control and not as a biological sample.

The control markers to be used include the following: sodium iodide, triethanolamine, tripropanolamine, tributanolamine, 2,5-dihydroxybenzoic acid, xylenol orange, hydroquinone sulfonic acid, cresol red ($C_{21}H_{17}NaO_5S$), and salts thereof.

Other non-limiting examples of control markers and their derivates include 3-[4-(hydroxyphenyl)amino]-3-oxopropanoic acid, N-acetyl-5-aminosalicyclic acid, N-ethyl-N-(3-sulfopropyl)-3-methylaniline (also referred to as TOPS), 3-(N-ethyl-3-methylanilino)-2-hydroxypropanesulfonic acid (also referred to as TOOS), 8-anilino-1-naphthalenesulfonic acid, 8-anilino-1-naphthalenesulfonic acid, 8-anilino-1-naphthalenesulfonic acid, 2-napthylamine 1-sulfonic acid, sodium diphenylamine-4-sulfonate, N-ethyl-N-(2-hydroxy-3-sulfopropyl)-3,5-dimethylaniline (also referred to as MAOS), and salts thereof. It is desirable that the control markers and their derivatives thereof have sufficient stability and solubility in the control solution as well as having an oxidizing potential in a desired range.

In one method, the sodium iodide may be used in combination with a phenothiazine mediator or phenoxazine mediator such as, for example, 3-(2',5'-disulfophenylimino)-3H-phenothiazine mediator. It is also contemplated that the control markers of 2,5-dihydroxybenzoic acid, xylenol orange, hydroquinone sulfonic acid and cresol red may also be used with a phenothiazine mediator or phenoxazine mediator such as, for example, 3-(2',5'-disulfophenylimino)-3H-phenothiazine. In one method, the triethanolamine may be used in combination with a ferricyanide-based mediator such as potassium ferricyanide. It also contemplated that the control markers of tripropanolamine and tributanolamine may be used in combination with a ferricyanide-based mediator such as potassium ferricyanide. It is contemplated that the above-identified controls makers may be used with other mediators.

In another method, 3-(2',5'-disulfophenylimino)-3H-phenothiazine may be used as a mediator with the following control markers: 3-[4-(hydroxyphenyl)amino]-3-oxopropanoic acid, N-acetyl-5-aminosalicyclic acid, N-ethyl-N-(3-sulfopropyl)-3-methylaniline (TOPS), 3-(N-ethyl-3-methylanilino)-2-hydroxypropanesulfonic acid (TOOS), 8-anilino-1-naphthalenesulfonic acid, 8-anilino-1-naphthalenesulfonic acid, 8-anilino-1-naphthalenesulfonic acid, 2-napthylamine 1-sulfonic acid, sodium diphenylamine-4-sulfonate or N-ethyl-N-(2-hydroxy-3-sulfopropyl)-3,5-dimethylaniline (MAOS), and salts thereof. It is contemplated that other compounds may be used as a mediator for these control markers and their derivatives including, for example, ferricyande, especially using the higher voltage potential compounds.

The difference between the currents measured at high and low voltages may be compared to indicate the presence of the internal reference characteristic of the control solution. In one non-limiting method, a Differential Index (DI) may be employed following current components relating to the analtye (e.g., glucose) and the control marker:

$$DI = i_{high\ volt}/i_{low\ volt} = (i_{int\ ref} + i_{glucose})/i_{glucose} = 1 + i_{int\ ref}/i_{glucose}$$

where $i_{high\ volt}$ is the current measured at the higher voltage
$i_{low\ volt}$ is the current measured at the lower voltage It follows that if the control marker is not present (such as in the blood samples), $i_{int\ ref}$ should be zero and the $i_{high\ volt}$ will be substantially the same as $i_{low\ volt}$. Thus, the DI value will typically approach 1 when the control marker is not present. The DI value in practice, however, may have values over 1 when the control marker is not present, especially when a lower glucose concentration is measured during a change from a low voltage to a higher voltage. In such a scenario, the control marker may have a higher DI than 1.

When the control marker is present, the value of DI will be greater than 1, depending on the amount of the control marker relative to the amount of analyte. If the amount of control marker added to the control solution provides a current similar to that from oxidizing the analyte-related mediator, the DI value may be generally about two times that from oxidizing the analyte-related mediator. The control marker may be included in an amount suitable for control solutions corresponding to a high analyte concentration.

It is typical to use several control solutions corresponding to low, normal, and high analyte concentration to test a glucose meter. If, for example, the amount of the control marker is chosen so that the DI value is 1.75 or greater for the highest analyte concentration in the control solution, the current from the control marker will be relatively large compared to the current for the analyte in the lowest analyte control solution. Then the same amount of the control marker used with a control solution having a low analyte concentration will provide an even higher value of DI. Such high DI values will provide higher confidence in the presence of a control solution, rather than a biological sample (e.g., whole blood). Clearly, a quantitative index such as the DI value has an advantage over the more qualitative methods of relying on the shape of the current versus time curve in the burn or read periods. The addition of a control solution oxidized at a higher voltage provides a result that is independent of the enzymatic reaction and the composition of the control solution.

In one embodiment, the amount of the control marker added to the control solution is related to the amount of analyte present. That is, the amount of the control marker in the control solution is proportional to the analyte concentration to maintain an approximately constant DI value. One method uses enough control marker to provide a DI of about 1.5 or higher when the maximum amount of an analyte (e.g., using about 300 mg/dL of glucose) is used. Then, the amount of the control marker is reduced so that control solutions containing lower analyte concentrations maintain a DI value of 1.5 or higher.

Adding a control marker to control solutions makes it possible to readily distinguish between control solutions and biological samples, and provides improved accuracy of the analysis. The above-identified control markers are oxidizable electrochemically at a desirable potential. It is important to understand that not all compounds oxidizable chemically are oxidizable electrochemically at an appropriate potential or at any oxidizable potential.

Other additives may include buffers, polymers, salts, dyes, anti-microbial agents, thickening agents, and surfactants. It is contemplated that other additives may be used.

The pH of the control solution is an important factor in the reaction in which glucose is oxidized by an enzyme, such as glucose oxidase. For the measurement of glucose, a pH of about 5 to about 7 is desirable when glucose oxidase is used, while a pH of about 6 to about 8 is preferred when glucose dehydrogenase used. A buffer is usually provided to assure that the oxidation of glucose proceeds at the expected rate. It is advantageous that the control marker and the buffer are separate components, with each serving a different function, thus enabling the optimization of each function (buffer and control marker) separately. The buffers may be chosen from those compatible with the enzymatic reagent. Examples include, but are not limited to, citrate buffer, phosphate buffer and amine-based buffers (e.g., HEPES, MOPS, TES, bis-Tris and Tris). It is contemplated that other buffers may be used.

The polymeric materials used to mimic the blood's fluidic properties may include polyethylene oxide, polyhydroxyethyl methacrylate, polyvinylpyrrolidone (PVP), Xanthan gum, in amounts of from about 0.5 or 1.0 to about 25 wt. %. The glucose is typically present in control solutions in the amounts equivalent to about 30 to 400 mg/dL, a range that spans the expected glucose content of blood samples.

It is contemplated that an anionic polymer may be added to the control solution as an additive. When a control marker includes an anionic polymer, it generates a much higher current signal than a non-ionic polymer. By having a higher current signal, better differentiation of the control solution from the fluid sample (e.g., blood) is obtained. Additionally, by having a higher current signal, the costs of the control solution is reduced because less control marker is needed.

Some non-limiting examples of anionic polymers that may be used in a control solution include carboxylic acids, sulfonic acids, phosphoric acids and salts of the same. Non-limiting examples of carboxylic acids include polyacrylic acid (PAA), polymaleic acid, carboxymethyl cellulose (CMC), an alternating methylvinylether/maleic anhydride copolymer such as Gantrez® from International Specialty Products, copolymers or salts thereof. Non-limiting examples of sulfonic acids include polystyrene sulfonic acid, polyvinyl sulfonic acid (PVS), copolymers or salts thereof. Non-limiting examples of phosphoric acids that may be used include polyvinylphosphoric acid, polyvinylphosphoric sodium salt, polyvinylphosphoric potassium salt, copolymers and salts thereof. The amount of polymeric charge in the anionic polymer is related to the structure of the polymer and also the amount of polymer in the control solution.

It is also contemplated that the anionic polymer may be included in the reagent on the test sensor in addition to, or instead of, being located in the control solution.

It is contemplated that a salt may be added to the control solution in an amount that increases the measured current of the control marker significantly. By increasing the current of the control marker, the differentiation between the control solution and the fluid sample (e.g., blood) is improved. Additionally, by increasing the current of the control marker, the amount of the control marker needed is reduced, which reduces the cost.

Some non-limiting examples of salts that may be contained in the control solution include chloride salts, phosphate salts, nitrate salts and sulfate salts. Non-limiting examples of chloride salts include sodium chloride, potassium chloride, ammonium chloride and calcium chloride. Non-limiting examples of phosphate salts include sodium phosphate, potassium phosphate, ammonium phosphate and calcium phosphate. Non-limiting examples of nitrate salts include sodium nitrate, potassium nitrate, ammonium nitrate and calcium nitrate. Non-limiting examples of sulfate salts include sodium sulfate, potassium salt, ammonium salt and calcium sulfate. It is contemplated that other salts may be used to increase the current of the control markers such as sodium acetate, sodium citrate and sodium succinate.

The control solution includes a sufficient amount of anionic polymer to increase the electrical current by at least 5% as compared to a control solution in the absence of an anionic polymer. It is desirable for the control solution to include a sufficient amount of anionic polymer to increase the electrical current by at least 10 or 20% as compared to a control solution in the absence of an anionic polymer. It is even more desirable for the control solution to include a sufficient amount of anionic polymer to increase the electrical current by at least 40 or 50% as compared to a control solution in the absence of an anionic polymer.

It is contemplated that an anionic polymer may be used with the salts in the control solution to increase the measured current of the control marker significantly.

By introducing a control marker oxidizable at a higher voltage than is used to oxidize the analyte-related mediator, it is necessary to apply the higher voltage at some point during the measurement protocol. Where two periods are used as described above in connection with FIGS. 2 and 3 (the "burn" and "read" periods), various combinations of potential steps within and across the burn and read periods may be used to provide both a DI value identifying the control solution and a current from which the analyte content of the control solution could be determined. In one method, a high voltage is applied during the burn period and a low voltage is applied during the read period. Thus, the Differential Index is:

$$DI = i_{burn}/i_{read}$$

When the control marker is present, the current measured during the burn period includes the current resulting from oxidization of the control marker plus the current resulting from oxidizing the analyte-related mediator. The current measured during the read period results only from oxidation of the analyte, since the voltage would be too low to oxidize the control marker. Thus, the ratio of burn current to read current reflects the value of the control marker current against the current of the analyte measurement.

Alternatively, both high and low voltages may be applied during the burn period to detect the presence of the control marker, while only a low voltage is used during the read period. This combination of potential steps still maintains the working principle of taking the ratio of the current from a high voltage to that from a low voltage. A distinct change in the current would be seen when a change is made from a low voltage to a high voltage, or vice versa. The low voltage need not be identical with that used in the read period to measure analyte. The comparative voltage may be merely lower than needed to oxidize the control marker. Since the burn period corresponds to a time when the sample is hydrating the reagents, the current may change during the burn period, as suggested in the generic diagram of FIG. 3. Consequently, it may be advantageous to make more than one excursion between high and low voltages to assure that the DI values are not affected by changes in the reagent availability during the burn period.

In another alternative method, a high voltage (i.e., one that oxidizes the control marker) is used during a portion of the read period. Thus, the DI may be determined during the read period by measuring the high and low currents only during the read period. This method may be advantageous in that any variation in reagent availability seen in the burn period is avoided. Again, using more than one excursion between low and high voltages may be advantageous.

In another method, frequent cycling of potential between high and low voltages is used to affect the shape of the current versus time during the read period, which is shown generically in FIG. 3. The curve typically shows a rapid decay of the current caused by the depletion of the reduced mediator at and near the electrode surface. Thus, the total analyte (e.g., glucose) content is determined by correlation with the diffusion-limited current, rather than measuring the total analyte in the control solution. It is evident that the time chosen as a measure of the glucose is important if consistent and accurate measurements are to be obtained.

The control solutions of the present invention include a control marker that is oxidized electrochemically at a potential greater than that needed to oxidize the analyte and also includes a predetermined amount of analyte. Since, for example, oxidation of the glucose-related mediator (e.g., potassium ferricyanide) requires a potential of 200 mV relative to the potential at the counter electrode of ferricyanide, the oxidation potential for the control marker should be at least 200 mV and more desirably at least 300 mV greater relative to the same counter electrode.

One method of examining the effect of adding a control marker to control solutions is using cyclic voltammetry. Instead of applying a fixed potential, a varying voltage is used, sweeping from negative to positive relative to the counter electrode.

Another method of examining the effect of adding a control marker to control solutions is gated amperometry that uses pulses. The use of a gated amperometric pulse sequence may include multiple duty cycles that may provide improved accuracy and precision to an analysis, while reducing the completion time of the analysis.

Figure 4:
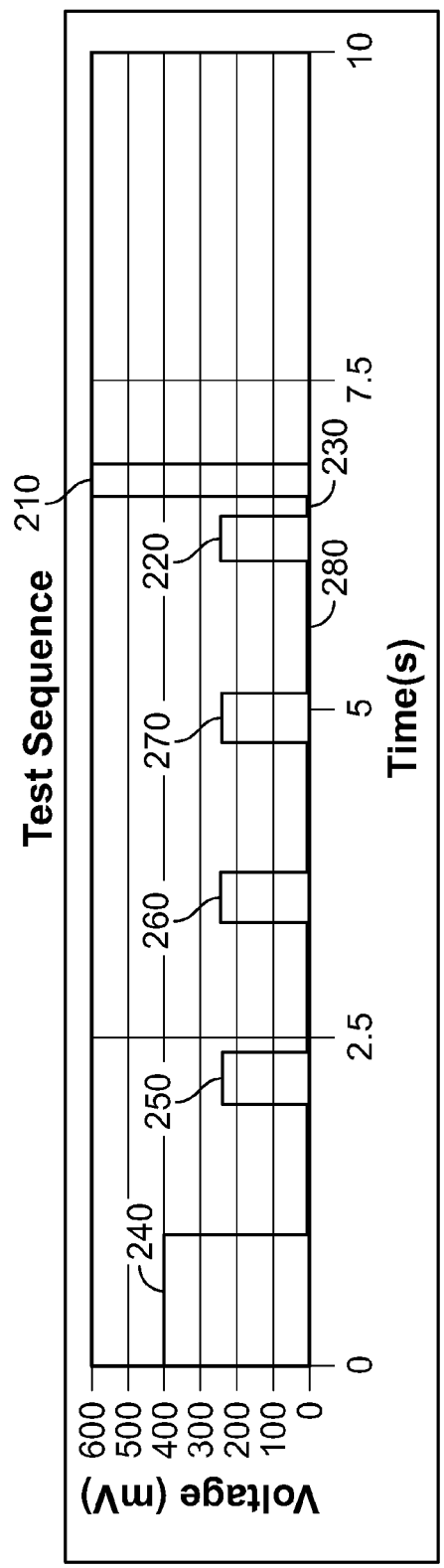
FIG. 4 is a plot of current versus time using gated amperometry according to one method.

One especially desirable gated amperometric method that may be used with the control markers identified above—sodium iodide, triethanolamine, tripropanolamine, tributanolamine, 2,5-dihydroxybenzoic acid, xylenol orange, hydroquinone sulfonic acid and cresol red—is shown in relation to FIG. 4. It is contemplated that this gated amperometric method may be used with other control markers identified above such as 3-[4-(hydroxyphenyl)amino]-3-oxopropanoic acid, N-acetyl-5-aminosalicyclic acid, N-ethyl-N-(3-sulfopropyl)-3-methylaniline (TOPS), 3-(N-ethyl-3-methylanilino)-2-hydroxypropanesulfonic acid (TOOS), 8-anilino-1-naphthalenesulfonic acid, 8-anilino-1-naphthalenesulfonic acid, 8-anilino-1-naphthalenesulfonic acid, 2-napthylamine 1-sulfonic acid, sodium diphenylamine-4-sulfonate, N-ethyl-N-(2-hydroxy-3-sulfopropyl)-3,5-dimethylaniline (MAOS), and salts thereof.

FIG. 4 shows one non-limiting example of such a desirable gated amperometric method. Specifically, in this method, at the end of the assay, a high voltage is raised at the end of the assay potential sequence. For example, FIG. 4 shows a high voltage segment 210 (600 mV) connected to a normal voltage pulse 220 (200 mV). Before this high voltage is raised, a separate short delay or relaxation period 230 for the control marker. This is shown at a time of from about 6 to about 7 seconds in FIG. 4. By having a separate short delay or relaxation period, this assists in reducing the likelihood to consume the reduced form of the mediator, which may result in the control markers having a lower current than expected. By having this relaxation period, the current of the control solution will have desirably higher currents that will better assist in differentiating the control solution and the actual analyte readings.

FIG. 4 depicts pulse sequences that include an initial cycle 240 followed by four duty cycles 250, 260, 270, 220 having the same excitation and open circuit delay times in addition to a terminal read pulse of longer duration that increases in voltage after a very short relaxation period. A duty cycle is defined herein as having a relaxation period followed by voltage pulse. The increased voltage of this terminal read pulse provides the ability to detect a species having a higher oxidation potential.

In this particular gated amperometric method, the analyte is measured by (a) applying a first potential sufficient to oxidize the analyte for a first predetermined period of time, followed by (b) applying pulsed second potentials insufficient to oxidize the analyte and lower than the first potential for a second predetermined period of time, and followed by (c) applying a third potential higher than the second potential and sufficient to oxidize the analyte for a third predetermined period of time. This third potential is applied after a very short relaxation period after, for example, one of the second potentials was applied.

Thus, in the FIG. 4 method, each duty cycle includes an excitation that may be provided at a relatively constant voltage. Each duty cycle also includes a relaxation period 280 that may be provided by an open circuit. The pulse sequences may reduce the time required for analysis by eliminating the need for additional delays and pulses, such as "incubation" delays to provide reagent rehydration, "burn-off" pulses to renew the electrodes and mediator regeneration pulses to renew the oxidation state of the mediator, thus reducing analysis time.

Even with shorter analysis times, the inventive gated amperometric pulse sequence may improve accuracy and/or precision in relation to conventional methods. In one aspect, errors in performance accuracy introduced by the hematocrit effect and precision introduced by varying cap-gap volume may be reduced with the assistance of the inventive pulse sequence. In another aspect, errors otherwise resulting from a non-steady-state sensor condition and/or mediator background may be reduced. The gated pulse sequences also may allow the determination of transient current and contour profiles that simulate a steady-state condition. The transient current profiles may be used to provide a plurality of sets of calibration constants, under-fill detection, and the ability to determine the temperature of the sample, instead of relying on the temperature from the measuring device.

The duty cycles may vary in the inventive gated amperometric pulse sequence. In one method, 3 to 18 or from 3 to 10 duty cycles are applied within about 30 seconds or less. In another method, from 3 to 8 duty cycles are applied within 3 to 16 seconds.

The potential applied during the excitation portion of the duty cycle is desirably applied at a substantially constant voltage and polarity throughout its duration. This directly contrasts to conventional read pulses where the voltage is changed or "swept" through multiple voltage potentials and/or polarities during data recordation. In one aspect, the duration of the excitation is at most 4 or 5 seconds, and desirably less than 3, 2, 1.5, or 1 second. In another aspect, the duration of the excitation is from 0.01 to 3 seconds, from 0.01 to 2 seconds, or from 0.01 to 1.5 seconds. More desirably, the duration of the excitation is from 0.1 to 1.2 seconds.

After the excitation period, the measuring device may open the circuit through the sensor strip, thus allowing the system to relax. During the relaxation period, the current present during the excitation period is substantially reduced by at least one-half, preferably by an order of magnitude, and more desirably to zero. Desirably, a zero current state is provided by an open circuit or other method known to those of ordinary skill in the art to provide a substantially zero current flow. At least 3 relaxations may be provided during the duty cycles of the pulse sequence.

In one aspect, the relaxation period is at least 10, 5, 3, 2, 1.5, 1, or 0.5 seconds in duration. In another aspect, the relaxation period is from 0.1 to 3 seconds, from 0.1 to 2 seconds, or from 0.1 to 1.5 seconds in duration. More desirably, the relaxation period is from 0.2 to 1.5 seconds in duration and provided by an open circuit.

During the relaxation period, the ionizing agent may react with the analyte to generate additional measurable species without the effects of an electric potential. Thus, for a glucose-sensor system including glucose oxidase and a ferricyanide mediator as reagents, additional ferrocyanide (reduced mediator) responsive to the analyte concentration of the sample may be produced without interference from an electric potential during the relaxation period.

According to another method, a control marker differentiation method is based on both DI discussed above and the current of the control marker. As discussed above, DI is as follows:

$$DI = i_{high\ volt}/i_{low\ volt} = (i_{int\ ref} + i_{glucose})/i_{glucose} = 1 + i_{int\ ref}/i_{glucose}$$

where $i_{high\ volt}$ is the current measured at the higher voltage $i_{low\ volt}$ is the current measured at the lower voltage The benefit of using both DI and the current of the control marker is to obtain better differentiation of the control solution and the fluid sample (e.g., blood sample) with very low glucose concentrations. Because blood samples with low glucose have a higher DI, they are more difficult to differentiate from the control marker when only DI is used.

In this method, the control current is checked after a certain time period (e.g., after 5 seconds at a current of 0.6V), which may be referred to as $i_{high\ volt}$. If the current is less than a selected value (e.g., 12,000 nA), then the sample is blood. If the current is greater than the selected value, DI is calculated. If DI is above a certain number (e.g., 1.3), then the sample being tested is a control solution and, if not, the sample is a blood sample. The DI uses a current measurement at a higher voltage and a lower voltage. At the lower voltage, only the current from the mediator being reduced is measured. At the higher voltage, the current from both the control marker and the mediator is measured.

EXAMPLES

The following examples illustrate the concept and application of control markers and its method for auto-detection of control solutions.

Example 1

Figure 5:
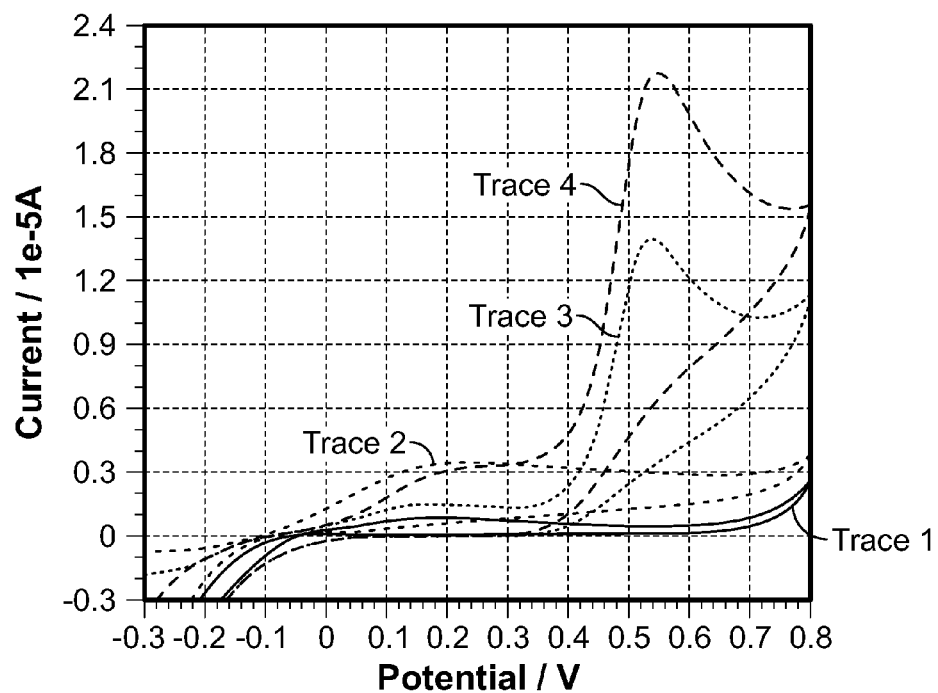
FIG. 5 is a cyclic voltammogram described in Example 1.

FIG. 5 showed the current plotted versus the potential as the potential difference was cycled between −300 mV and +800 mV at 25 mV/sec using carbon electrodes. The testing was performed on an electrochemical work station of CH Instrument Co.

As shown in FIG. 5, Traces 1-4 represented the cyclic voltammograms of sodium iodide (NaI) from a solution running at the 3-(2′,5′-disulfophenylimino)-3H-phenothiazine-based sensor. This sensor had the above mediator deposited on both the working and counter electrodes. When there is no NaI in the solution feeding to the sensor, the cyclic voltammogram resulted from the mediator. Otherwise, the cyclic voltammogram was the sum of both the mediator (appears at lower potential) and the control marker NaI.

Trace 1 included 0 mg/dl of glucose, while Trace 2 used 350 mg/dl of glucose. There were no control markers used in Traces 1 and 2. As shown in FIG. 5, there were no additional oxidation peaks in Traces 1 and 2 after the initial oxidation started at about 0 volts. Traces 3 included 0 mg/dL of glucose and 50 mV NaI as the control marker, while Trace 4 used 350 mg/dl of glucose and 50 mV NaI. Traces 3 and 4 represented the oxidation wave of NaI in the solution. Both of the measured currents peaked in the potential range between about 500 and 600 mV for Traces 3 and 4. As shown in FIG. 5, there was no oxidation current from the NaI in the potential range of 100 to 300 mV. Thus, a low voltage at a potential in the range of about 200 to 300 mV for the mediator (3-(2',5'-disulfophenylimino)-3H-phenothiazine) and a high voltage at a potential range in the range of about 500 to 600 mV for the control marker (NaI) may be applied such that there is no overlap between the mediator's oxidation and the control marker's oxidation.

Example 2

Figure 6:
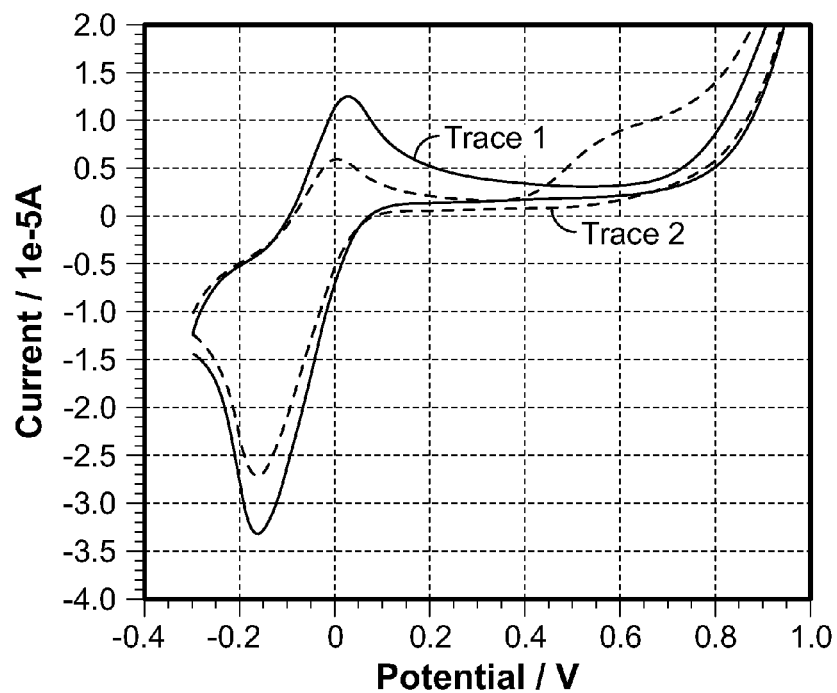
FIG. 6 is a cyclic voltammogram described in Example 2.

FIG. 6 showed the current plotted versus potential as the potential difference was cycled between −400 mV and +1,000 mV at 25 mV/sec using carbon electrodes. The testing was performed on an electrochemical work station of CH Instrument Co.

As shown in FIG. 6, Trace 1 and 2 represented cyclic voltammograms of triethanolamine (TEA) and ferricyanide in a potassium ferricyanide-based glucose mediator. The sensor with ferricyanide mediator was manufactured with deposition of mediator ferricyanide, enzyme, polymer and other ingredients. Trace 1 included 75 mg/dl of glucose, but did not use a control marker. As shown in FIG. 6, there was an apparent peak in Trace 1 around 0 mV, but no oxidation peak at 600 mV. In addition to the 75 mg/dL of glucose, Trace 2 further included 50 mV triethanolamine as the control marker or the internal reference. In contrast to Trace 1, Trace 2 with the triethanolamine had a cyclic voltammogram that displayed oxidation currents of various magnitudes of 400 mV and greater. See FIG. 6. Thus, since the peak at 0 mV is well separated from the currents using triethanolamine, a low voltage having a potential in the range of about 200 mV to 300 mV for the mediator (potassium ferricyanide) and a high voltage at a potential of about 600 mV for the control marker (triethanolamine) may be applied such that there is no overlap between the mediator's oxidation and the control marker's oxidation.

Example 3

Figure 7:
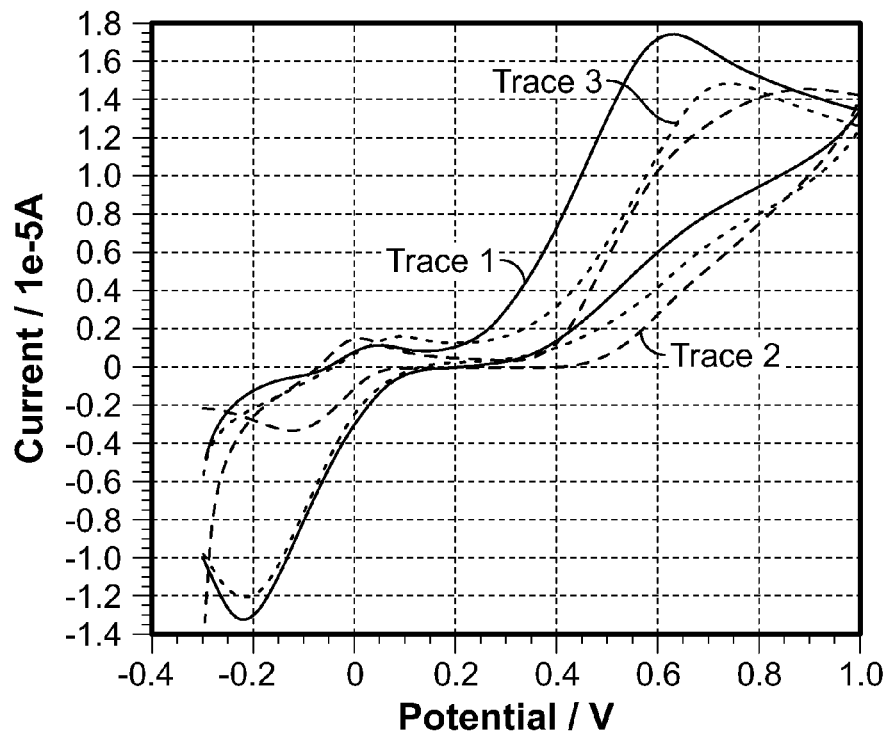
FIG. 7 is a cyclic voltammogram described in Example 3.

FIG. 7 shows the current plotted versus potential as the potential difference was cycled between −400 mV and +1,000 mV at 25 mV/sec using carbon electrodes. The testing was performed on an electrochemical work station of CH Instrument Co.

As shown in FIG. 7, Traces 1-3 represented cyclic voltammograms of three control markers from a solution running at the 3-(2',5'-disulfophenylimino)-3H-phenothiazine-based sensor. This sensor has the above mediator deposited on both the working and counter electrodes from manufacturing. Each trace contained the oxidation of both the reduced mediator and the control marker. Trace 1 further included 50 mV of 2,5-dihydroxybenzoic acid at pH 7 as the control marker. Trace 2 further included 50 mV of xylenol orange at pH 7 as the control marker. Trace 3 further included 50 mV of hydroquinone sulfonic acid at pH 7 as the control marker.

Referring still to FIG. 7, the small redox waves near 0 mV corresponded with the oxidation of the 3-(2',5'-disulfophenylimino)-3H-phenothiazine mediator in the electrochemical test sensors. This was also shown in Traces 1 and 2 of FIG. 5 that were discussed above. Referring back to FIG. 7, the oxidation potentials of each of the three chemical species (2,5-dihydroxybenzoic acid, xylenol orange and hydroquinone sulfonic acid) were about 400 to 600 mV higher as shown in FIG. 7 by respective Traces 1-3. Thus, a low voltage at a potential of about 200 mV for the mediator (3-(2',5'-disulfophenylimino)-3H-phenothiazine) and a high voltage at a potential in the range of about 600 to 800 mV for the control markers (2,5-dihydroxybenzoic acid, xylenol orange and hydroquinone sulfonic acid) may be applied such that there is no overlap between the mediator's oxidation and the control marker's oxidation.

Example 4

Figure 8:
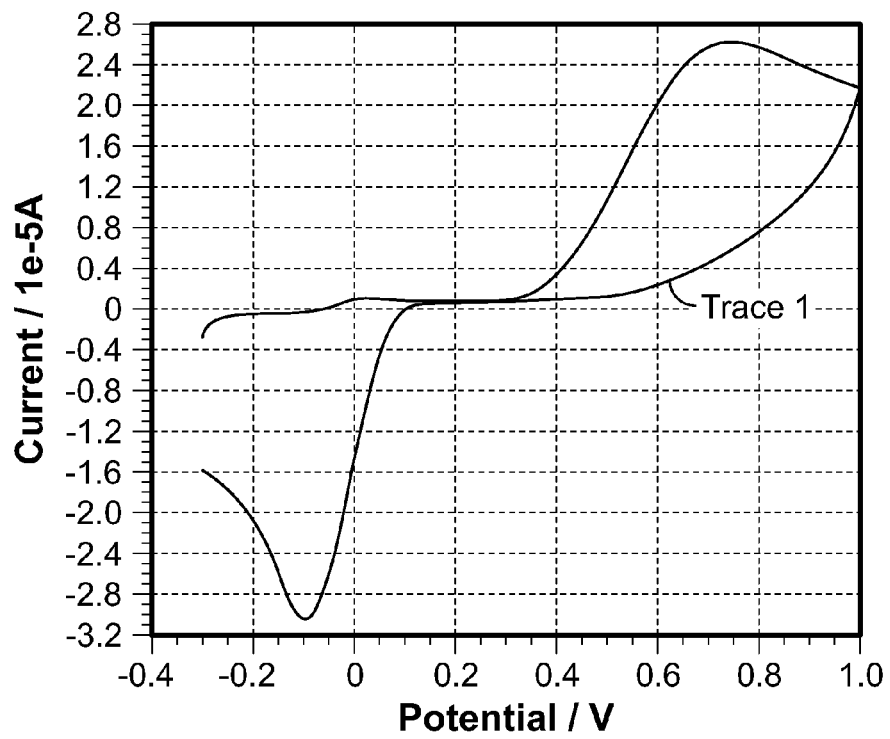
FIG. 8 is a cyclic voltammogram described in Example 4.

FIG. 8 shows the current plotted versus potential as the potential difference was cycled between −400 mV and +1,000 mV at 25 mV/sec using carbon electrodes. The testing was performed on an electrochemical work station of CH Instrument Co.

As shown in FIG. 8, Trace 1 represented the cyclic voltammogram of tripropanolamine (TPA) and ferricyanide in the potassium ferricyanide-based sensor. The sensor with ferricyanide mediator was manufactured with deposition of mediator ferricyanide, enzyme, polymer and other ingredients. The small redox waves near 0 mV indicated that the oxidation of ferrocyanide and the reduction of ferricyanide in the sensor. This was also shown in Trace 1 of FIG. 6 that was discussed above. Referring back to FIG. 8, the oxidation potential of the chemical species (tripropanolamine) was about 600 to 700 mV higher than ferricyanide as shown in FIG. 8 by Trace 1. Thus, a low voltage at a potential of about 200 mV for the mediator (ferricyanide) and a high voltage at a potential in the range of about 600 to 700 mV for the control marker (tripropanolamine) may be applied such that there is no overlap between the mediator's oxidation and the control marker's oxidation.

Example 5

Figure 9:
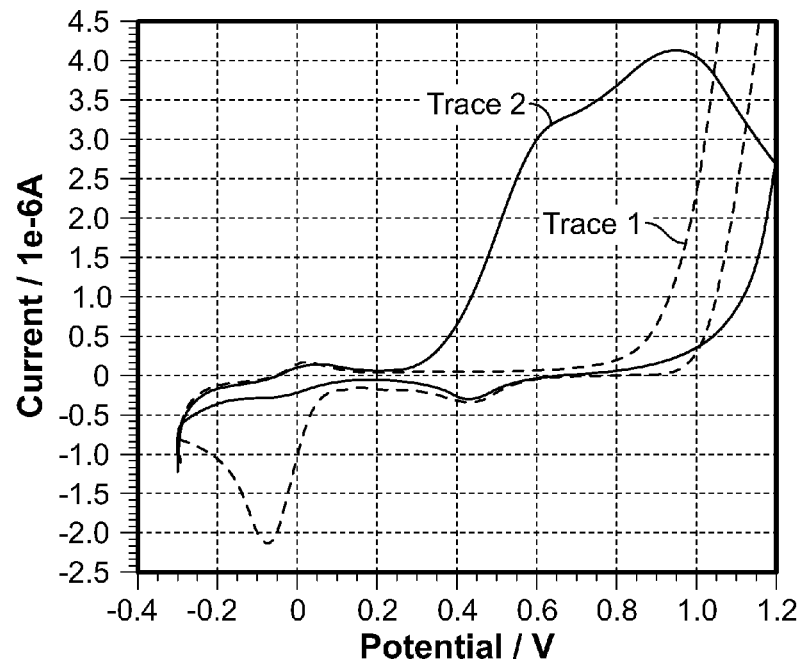
FIG. 9 is a cyclic voltammogram described in Example 5.

FIG. 9 shows the current plotted versus potential as the potential difference was cycled between −400 mV and +1,200 mV at 25 mV/sec using carbon electrodes. The testing was performed on an electrochemical work station of CH Instrument Co.

As shown in FIG. 9, Traces 1 and 2 represented cyclic voltammograms of Cresol Red from a solution running at the 3-(2',5'-disulfophenylimino)-3H-phenothiazine-based sensor. This sensor has the above mediator deposited on both the working and counter electrodes from manufacturing. When there is no Cresol Red in the solution feeding to the sensor, the cyclic voltammogram resulted from the mediator. Otherwise, the cyclic voltammogram is the sum of both the mediator (appears at lower potential) and the control marker Cresol Red. Trace 1 included 3-(2',5'-disulfophenylimino)-3H-phenothiazine mediator, but did not include a control marker or internal reference. Trace 2 included 3-(2',5'-disulfophenylimino)-3H-phenothiazine mediator and included 100 mV of cresol red.

Referring still to FIG. 9, the small redox waves near 0 mV corresponded with the oxidation of the 3-(2',5'-disulfophenylimino)-3H-phenothiazine mediator in the electrochemical test sensors. This was also shown in Traces 1 and 2 of FIG. 5 that were discussed above. Referring back to FIG. 9, the oxidation potential of the cresol red was about 400 to 600 mV higher as shown in FIG. 9 by comparing respective Traces 1 and 2. Thus, a low voltage at a potential of about 200 mV for the mediator (3-(2',5'-disulfophenylimino)-3H-phenothiazine) and a high voltage at a potential in the range of about 400 to 600 mV for the cresol red may be applied such that there is no overlap between the mediator's oxidation and the control marker's oxidation.

Example 6

Figure 10:
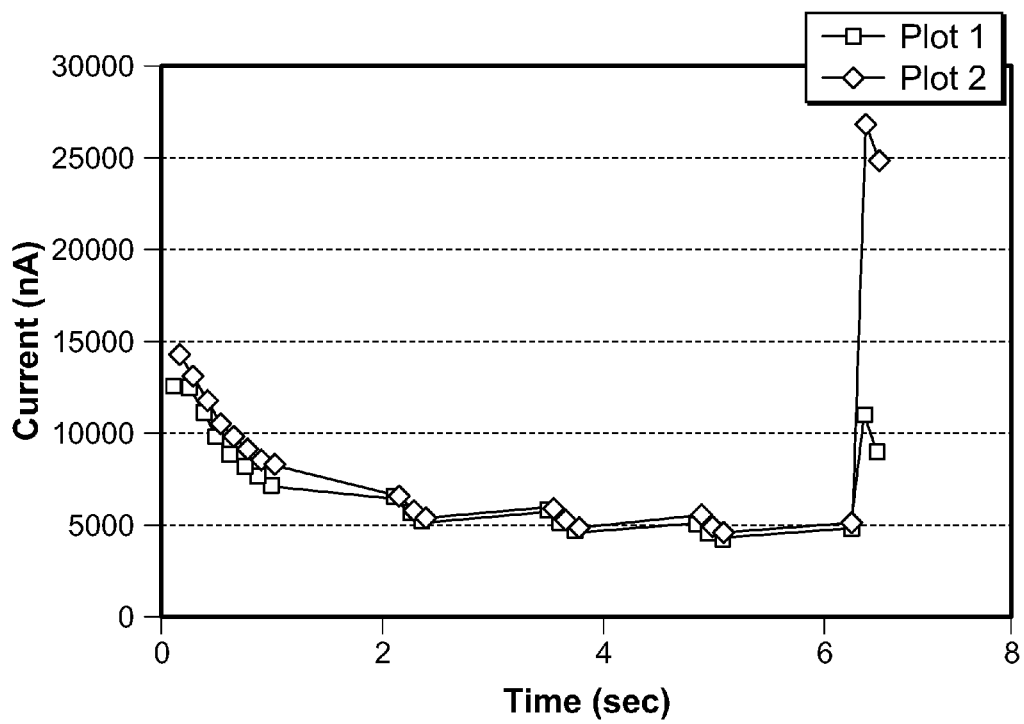
FIG. 10 is a plot of current versus time obtained in Example 6.

Referring to FIG. 10, a plot of current (in nA) versus time (in seconds) is shown with a solution including a control marker and a solution that does not include control marker. An aqueous solution containing 350 mg/dl glucose (Plot 1) was compared with another solution containing 350 mg/dL glucose and 50 mV sodium iodide (NaI) as the control marker (Plot 2). Each of the solutions contained 100 mV of (2',5'-disulfophenylimino)-3H-phenothiazine mediator. This mediator was located on both of the counter and working electrodes of the test sensors.

The current applied in FIG. 10 was the same cyclic voltammetry method described as described above with respect to FIG. 4. Specifically, an initial voltage of 400 mV was applied at time 0. This was following by three separate normal pulses of 200 mV was applied at times of about 2.2, 3.5 and 4.8 seconds. At the end of the assay, a high voltage is raised at the end of the assay potential sequence. A normal voltage pulse of 200 mV was applied at about 6.2 seconds following by a very short delay or relaxation period before a high voltage of 600 mV was applied at about 6.3 seconds.

As shown in FIG. 10, the current sequence at the end of the assay showed a much high current for Plot 2 (with sodium iodide) than with Plot 1 (without a control marker). Compare current of 25000 nA of Plot 2 with current of about 11000 nA of Plot 1 at time 6.2 seconds Thus, the use of the control marker of NaI can be differentiated from a solution without the control marker NaI.

Example 7

Figure 11:
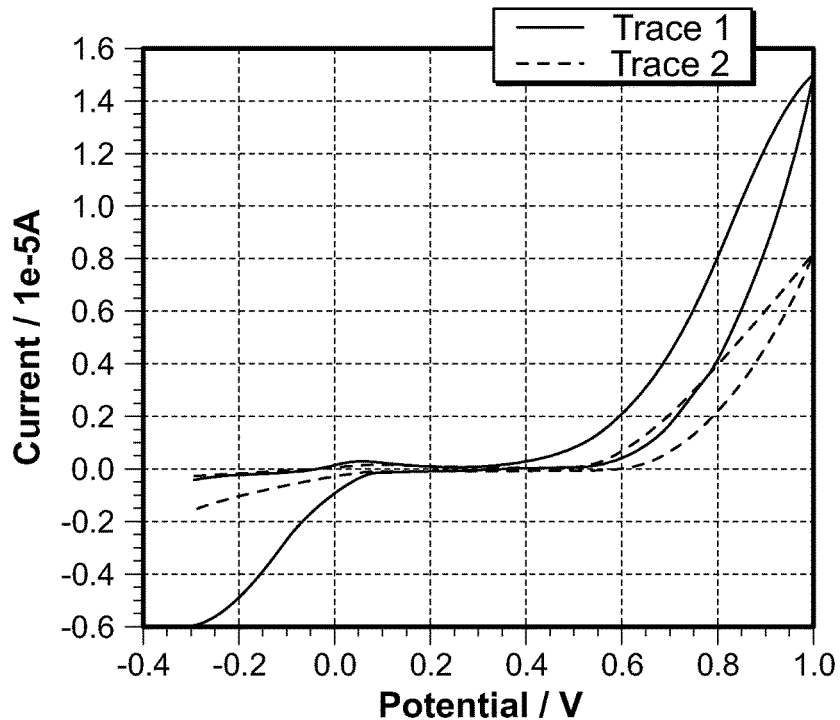
FIG. 11 are cyclic voltammograms described in Example 7.

FIG. 11 shows the current plotted versus potential as the potential difference was cycled between −400 mV and +1,000 mV at 25 mV/sec using carbon electrodes. The testing was performed on an electrochemical work station of CH Instrument Co.

As shown in FIG. 11, Trace 1 represented the cyclic voltammogram of 50 mV 3-[4-(hydroxyphenyl)amino]-3-oxopropanoic acid. The sensor with a (2',5'-disulfophenylimino)-3H-phenothiazine ferricyanide mediator was manufactured with deposition of the (2',5'-disulfophenylimino)-3H-phenothiazine mediator, enzyme, polymer and other ingredients. The redox waves near and below 0 mV indicated that the oxidation and reduction of the mediator in the sensor. The oxidation potential of the chemical species (3-[4-(hydroxyphenyl)amino]-3-oxopropanoic acid) was about 600 to 800 mV higher than the (2',5'-disulfophenylimino)-3H-phenothiazine as shown in FIG. 11 by Trace 1. Thus, a low voltage at a potential of about 200 mV for the mediator and a high voltage at a potential in the range of about 600 to 700 mV for the control marker (3-[4-(hydroxyphenyl)amino]-3-oxopropanoic acid) may be applied such that there is no overlap between the mediator's oxidation and the control marker's oxidation.

Having a voltage about 0.6V is highly desirable because this differentiates from the mediator's oxidation while still having a lower oxidation potential that reduces the likelihood of oxidizing other components in the fluid (e.g., blood). In other words, the higher the potential, the more likelihood that other components in the fluid will be oxidized.

Still referring to FIG. 11, Trace 2 represented the cyclic voltammogram of 30 mV N-acetyl-5-aminosalicyclic acid (AAS) and the mediator (2',5'-disulfophenylimino)-3H-phenothiazine. The sensor included the mediator, enzyme, polymer and other ingredients. The small redox waves near 0 mV indicated the oxidation and reduction of the mediator in the sensor. The oxidation potential of the chemical species (N-acetyl-5-aminosalicyclic acid) was about 600 to 800 mV higher than the mediator as shown in FIG. 11 by Trace 2. Thus, a low voltage at a potential of about 200 mV for the mediator and a high voltage at a potential in the range of about 600 to 700 mV for the control marker (N-acetyl-5-aminosalicyclic acid) may be applied such that there is no overlap between the mediator's oxidation and the control marker's oxidation.

Example 8

Figure 12:
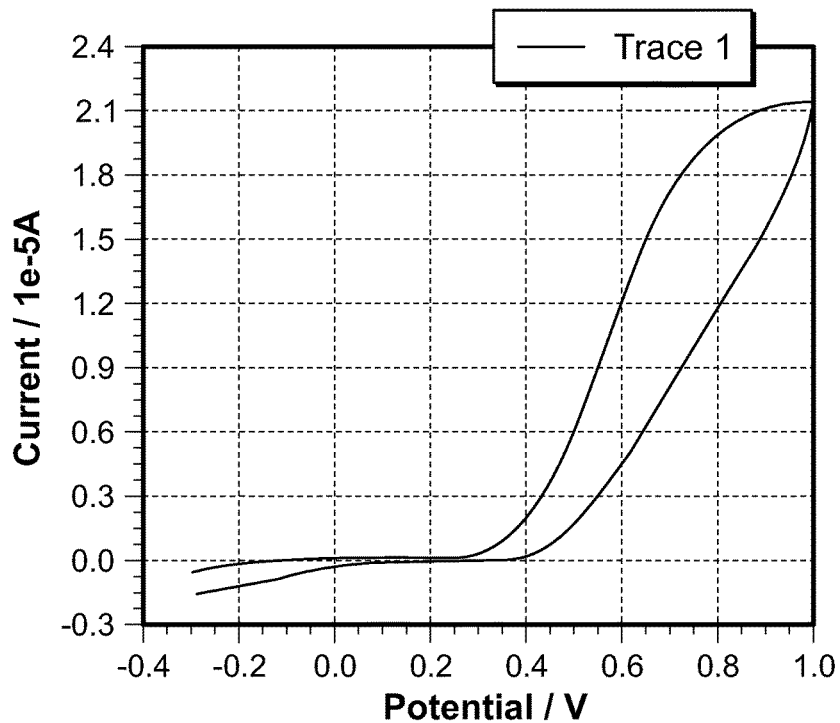
FIG. 12 is a cyclic voltammogram described in Example 8.

FIG. 12 shows the current plotted versus potential as the potential difference was cycled between −400 mV and +1,000 mV at 25 mV/sec using carbon electrodes. The testing was performed on an electrochemical work station of CH Instrument Co.

As shown in FIG. 12, Trace 1 represented the cyclic voltammogram of 50 mV N-ethyl-N-(3-sulfopropyl)-3-methylaniline (TOPS) and the mediator (2',5'-disulfophenylimino)-3H-phenothiazine. The sensor included the mediator, enzyme, polymer and other ingredients. The small redox waves near 0 mV indicated the oxidation and reduction of the mediator in the sensor. The oxidation potential of the chemical species (N-ethyl-N-(3-sulfopropyl)-3-methylaniline) was about 400 to 800 mV higher than the mediator as shown in FIG. 12 by Trace 1. Thus, a low voltage at a potential of about 200 mV for the mediator and a high voltage at a potential in the range of about 400 to 800 mV for the control marker (N-ethyl-N-(3-sulfopropyl)-3-methylaniline) may be applied such that there is no overlap between the mediator's oxidation and the control marker's oxidation.

Example 9

Figure 13:
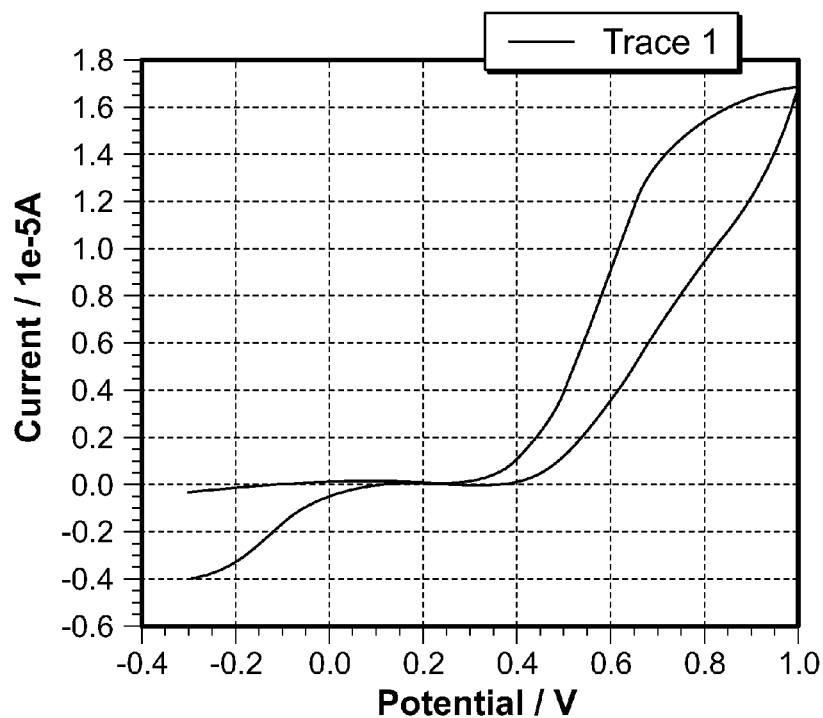
FIG. 13 is a cyclic voltammogram described in Example 9.

FIG. 13 shows the current plotted versus potential as the potential difference was cycled between −400 mV and +1,000 mV at 25 mV/sec using carbon electrodes. The testing was performed on an electrochemical work station of CH Instrument Co.

As shown in FIG. 13, Trace 1 represented the cyclic voltammogram of 50 mV 3-(N-ethyl-3-methylanilino)-2-hydroxypropanesulfonic acid sodium salt (TOOS) and the mediator (2',5'-disulfophenylimino)-3H-phenothiazine. The sensor was manufactured with deposition of the mediator, enzyme, polymer and other ingredients. The redox waves near 0 mV indicated the oxidation and reduction of the (2',5'-disulfophenylimino)-3H-phenothiazine in the sensor. The oxidation potential of the chemical species (3-(N-ethyl-3-methylanilino)-2-hydroxypropanesulfonic acid sodium salt) was about 400 to 800 mV higher than the mediator as shown in FIG. 13 by Trace 1. Thus, a low voltage at a potential of about 200 mV for the mediator and a high voltage at a potential in the range of about 400 to 800 mV for the control marker (3-(N-ethyl-3-methylanilino)-2-hydroxypropanesulfonic acid sodium salt) may be applied such that there is no overlap between the mediator's oxidation and the control marker's oxidation.

Example 10

Figure 14:
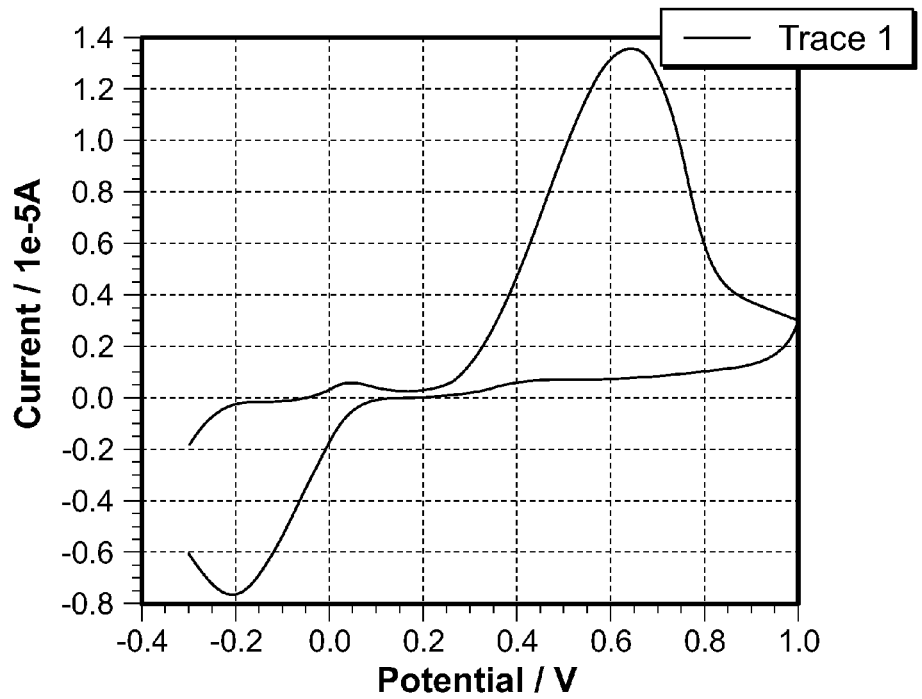
FIG. 14 is a cyclic voltammogram described in Example 10.

FIG. 14 shows the current plotted versus potential as the potential difference was cycled between −400 mV and +1,000 mV at 25 mV/sec using carbon electrodes. The testing was performed on an electrochemical work station of CH Instrument Co.

As shown in FIG. 14, Trace 1 represented the cyclic voltammogram of 50 mV 8-anilino-1-naphthalenesulfonic acid and the mediator (2',5'-disulfophenylimino)-3H-phenothiazine. The sensor was manufactured with deposition of the mediator, enzyme, polymer and other ingredients. The large redox waves near 0 mV indicated the oxidation and reduction of the mediator in the sensor. The oxidation potential of the chemical species (8-anilino-1-naphthalenesulfonic acid) was about 250 to 400 mV higher than the mediator as shown in FIG. 14 by Trace 1. Thus, a low voltage at a potential of about 150 mV for the mediator and a high voltage at a potential in the range of about 350 to 400 mV for the control marker (8-anilino-1-naphthalenesulfonic acid) may be applied such that there is no overlap between the mediator's oxidation and the control marker's oxidation.

Example 11

Figure 15:
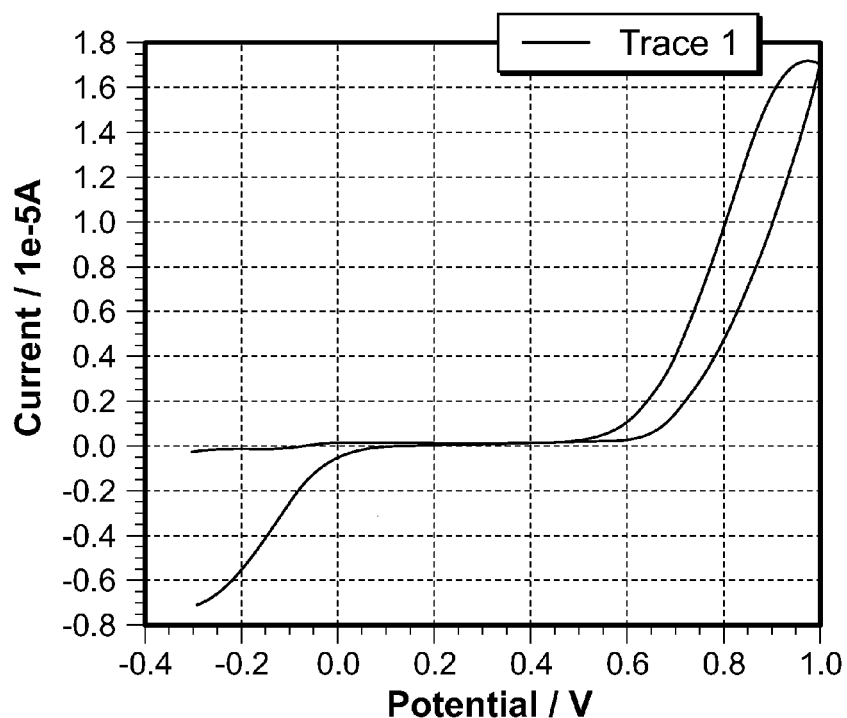
FIG. 15 is a cyclic voltammogram described in Example 11.

FIG. 15 shows the current plotted versus potential as the potential difference was cycled between −400 mV and +1,000 mV at 25 mV/sec using carbon electrodes. The testing was performed on an electrochemical work station of CH Instrument Co.

As shown in FIG. 15, Trace 1 represented the cyclic voltammogram of 50 mV 2-napthylamine 1-sulfonic acid and the mediator (2',5'-disulfophenylimino)-3H-phenothiazine. The sensor was manufactured with deposition of the mediator, enzyme, polymer and other ingredients. The large redox waves near 0 mV indicated that the oxidation and reduction of the mediator in the sensor. The oxidation potential of the chemical species (2-napthylamine 1-sulfonic acid) was about 600 to 800 mV higher than the mediator as shown in FIG. 15 by Trace 1. Thus, a low voltage at a potential of about 200 mV for the mediator and a high voltage at a potential in the range of about 600 to 800 mV for the control marker (2-napthylamine 1-sulfonic acid) may be applied such that there is no overlap between the mediator's oxidation and the control marker's oxidation.

Example 12

Figure 16:
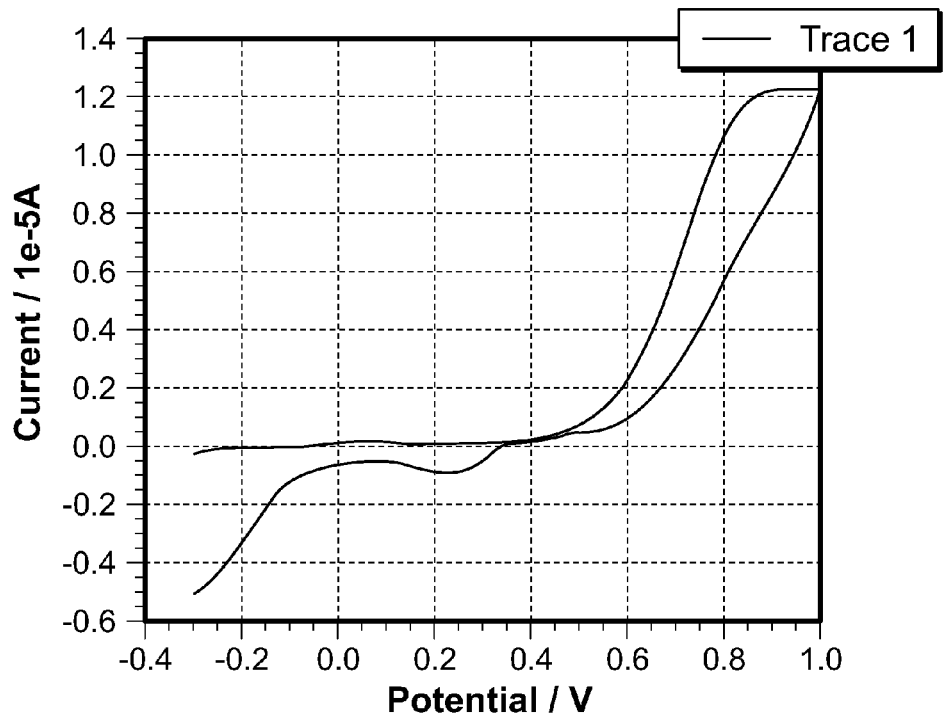
FIG. 16 is a cyclic voltammogram described in Example 12.

FIG. 16 shows the current plotted versus potential as the potential difference was cycled between −400 mV and +1,000 mV at 25 mV/sec using carbon electrodes. The testing was performed on an electrochemical work station of CH Instrument Co.

As shown in FIG. 16, Trace 1 represented the cyclic voltammogram of 50 mV sodium diphenylamine-4-sulfonate and the mediator (2',5'-disulfophenylimino)-3H-phenothiazine. The sensor was manufactured with deposition of the mediator, enzyme, polymer and other ingredients. The large redox waves near 0 mV indicated the oxidation and reduction of the mediator in the sensor. The oxidation potential of the chemical species (sodium diphenylamine-4-sulfonate) was about 600 to 800 mV higher than the mediator as shown in FIG. 16 by Trace 1. Thus, a low voltage at a potential of about 300 mV for the mediator and a high voltage at a potential in the range of about 600 to 800 mV for the control marker (sodium diphenylamine-4-sulfonate) may be applied such that there is no overlap between the mediator's oxidation and the control marker's oxidation.

Example 13

Various examples showing the effect of current measurements with anionic polymers are discussed below. Specifically, the addition of an anionic polymer was shown to increase the current generated by the control solution. First and second solutions of 75 mV 3-(N-ethyl-3-methylanilino)-2-hydroxypropanesulfonic acid sodium salt (TOOS) included a non-ionic polymer-polyvinylpyrrolidone (PVP). A third solution included 11.6 mM of TOOS was included with the anionic polymer polyacrylic acid (PAA). The percentages of the polymers were selected to generally mimic the viscosity of the blood. The voltage was applied in on-off pulse sequences in which the testing period concluded with the voltage being raised to 0.6V.

TABLE 1

| Solution # | Control Solution | Polymer | Current @ 0.6 V (nA) |
|---|---|---|---|
| 1 | 75 mM TOOS | 1.7% PVP 10K | 16,518 |
| 2 | 75 mM TOOS | 6% PVP 6K | 17,867 |
| 3 | 11.6 mM TOOS | 18.7% PAA 3K | 21,597 |

As shown in Table 1, despite having a TOOS concentration over 6 times greater, Solutions 1 and 2 without an anionic polymer had a lower current than Solution 3, which included the anionic polymer PAA.

Table 2 below shows various currents that were measured at 0.6V (nA) with various solutions. The voltage was applied in on-off pulse sequences in which the testing period concluded with the voltage being raised to 0.6V. The pulse sequences were the same for the testing of each of the solutions. Solutions 4 and 5 included a non-ionic polymer-polyvinyl alcohol (PVA) and polyvinylpyrrolidone (PVP), respectively. Solutions 6 and 7, on the other hand, included an anionic polymer-polyvinyl sulfonic acid (PVS) and polyacrylic acid (PAA), respectively. The percentages of the polymer were selected to generally mimic the viscosity of the blood. Solutions 4-7 each included 10 mV of 3-(N-ethyl-3-methylanilino)-2-hydroxypropanesulfonic acid sodium salt (TOOS).

TABLE 2

| Solution # | Control Solution | Polymer | Current @ 0.6 V (nA) |
|---|---|---|---|
| 4 | 10 mM TOOS | 6% PVA 6K | 8,500 |
| 5 | 10 mM TOOS | 2.3% PVP 55K | 7,000 |
| 6 | 10 mM TOOS | 17.6% PVS | 15,500 |
| 7 | 10 mM TOOS | 18.7% PAA 3K | 16,000 |

As shown in Table 2, using the same amount of TOOS, Solutions 6 and 7 with an anionic polymer had much higher currents than Solutions 4 and 5, which did not include an anionic polymer. Compare 15,500 and 16,000 nA of Solutions 6 and 7 with 8,500 and 7,000 nA of Solutions 4 and 5.

Table 3 below shows various currents that were measured at 0.8V (nA) with various solutions. The voltage was applied in on-off pulse sequences in which the testing period concluded with the voltage being raised to 0.8V. The pulse sequences were the same for the testing of each of the solutions. Solutions 8-10 included non-ionic polymers-polyvinylpyrrolidone (PVP), 50 mV HEPES buffer, and polyvinyl alcohol (PVA), respectively. Solutions 11 and 12, on the other hand, included an anionic polymer-polyvinyl sulfonic acid (PVS) and polyacrylic acid (PAA), respectively. The voltage was applied in on-off pulse sequences in which the testing period concluded with the voltage being raised to 0.8V. Solutions 8-12 each included 10 mV of sodium diphenylamine-4-sulfonate (SDPAS).

TABLE 3

| Solution # | Control Solution | Polymer | Current @ 0.8 V (nA) |
|---|---|---|---|
| 8 | 10 mM SDPAS | 2.3 PVP 55K | 7,312 |
| 9 | 10 mM SDPAS | 50 mM HEPES buffer | 9,603 |
| 10 | 10 mM SDPAS | 6% PVA | 10,552 |
| 11 | 10 mM SDPAS | 17.6% PVS | 21,500 |
| 12 | 10 mM SDPAS | 18.7% PAA 3K | 21,600 |

As shown in Table 3, Solutions 11 and 12 with an anionic polymer had much higher currents than Solutions 8-10, which did not include an anionic polymer. Compare 21,500 and 21,600 nA of Solutions 11 and 12 with 7,312, 9,603 and 10,552 nA of Solutions 8-10.

Table 4 below shows various currents that were measured at 0.6V (nA) with various solutions. The voltage was applied in on-off pulse sequences in which the testing period concluded with the voltage being raised to 0.6V. The pulse sequences were the same for the testing of each of the solutions. Solution 13 included a non-ionic polymer-polyvinylpyrrolidone (PVP). Solution 14, on the other hand, included an anionic polymer-polyacrylic acid (PAA). The voltage was applied in on-off pulse sequences in which the testing period concluded with the voltage being raised to 0.6V. Solutions 13 and 14 each included 50 mV of HEPES.

TABLE 4

| Solution # | Control Solution | Polymer | Current @ 0.6 V (nA) |
|---|---|---|---|
| 13 | 15 mM TOOS | 16% PVP 2.4K | 9,480 |
| 14 | 15 mM TOOS | 18.7% PAA 2K | 20,788 |

As shown in Table 4, Solution 14 with an anionic polymer had a much higher current than Solution 13, which did not include an anionic polymer. Compare 20.788 nA of Solution 14 with 9,480 nA of Solution 13. Thus, anionic polymers, including PAA, increase the control marker current not because of its high polymer concentration, but rather because of the nature of its polymeric charge.

Example 14

Figure 17:
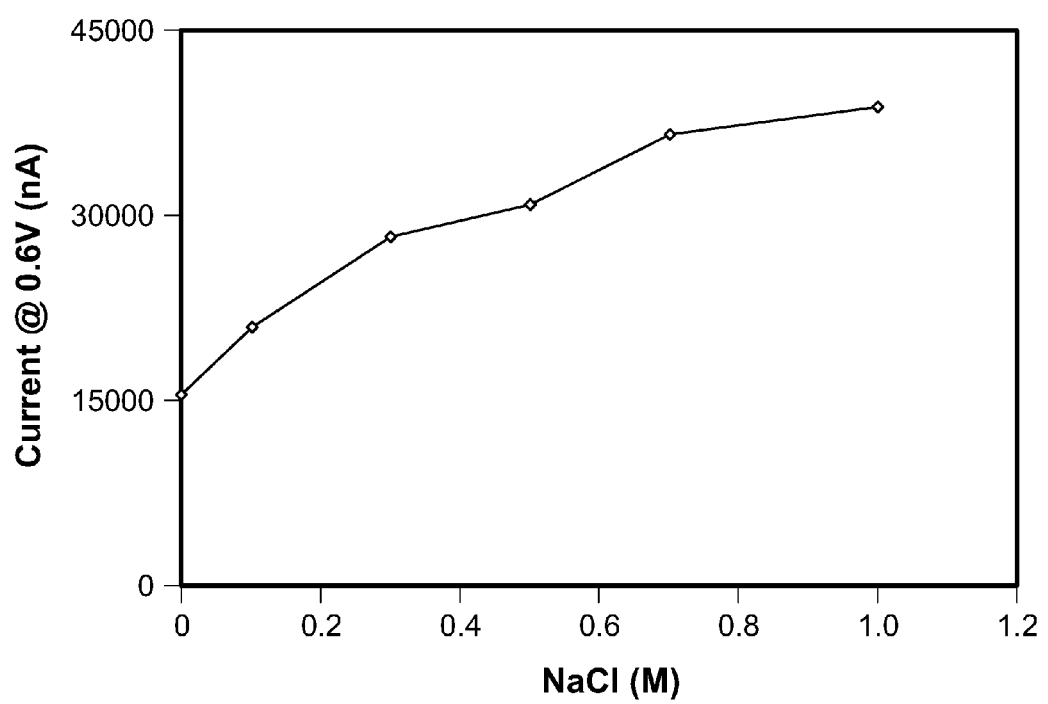
FIG. 17 is a plot of NaCl with a control marker described in Example 14.

Referring to FIG. 17, the current (in nA) was plotted against a control solution including several concentrations on sodium chloride (NaCl). The tested control solution included 50 mV of 3-(N-ethyl-3-methylanilino)-2-hydroxypropanesulfonic acid sodium salt (TOOS), 2.3% of polyvinylpyrrolidone and a buffer of 50 mV HEPES at a pH of 7. The current was taken at 5.3 seconds in an on-off pulse sequence with the voltage being 0.6V. Specifically, there were six different solutions of NaCl that were tested –0M, 0.1M, 0.3 M, 0.5 M, 0.7 M and 1 M. As shown in FIG. 17, the measured current increased significantly as the amount of sodium chloride was increased in the control solution.

Example 15

Figure 18A:
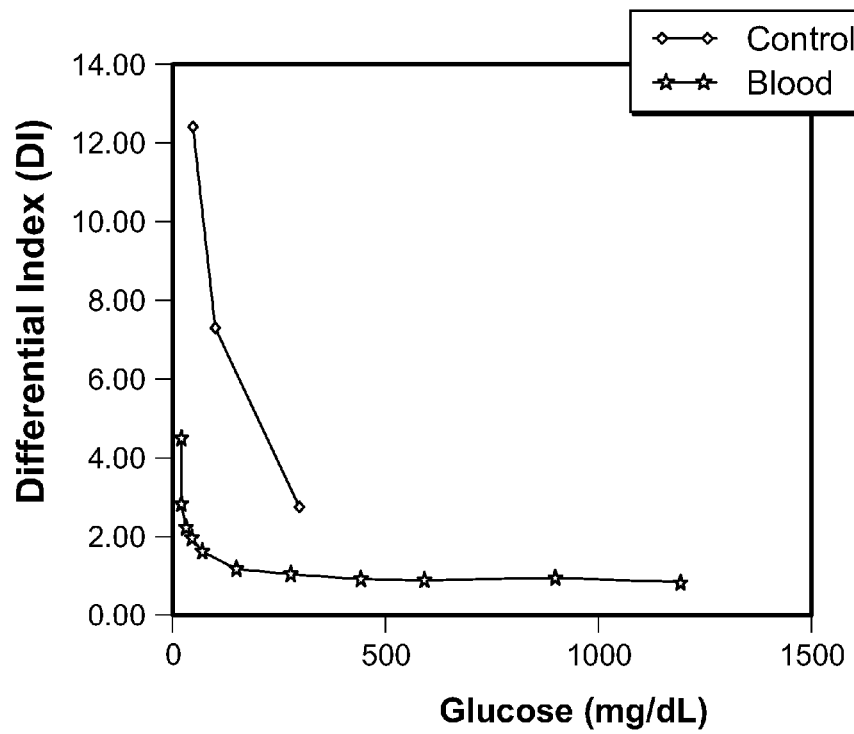
FIGS. 18A, 18B are plots of control solutions and blood solutions described in Example 15.
Figure 18B:
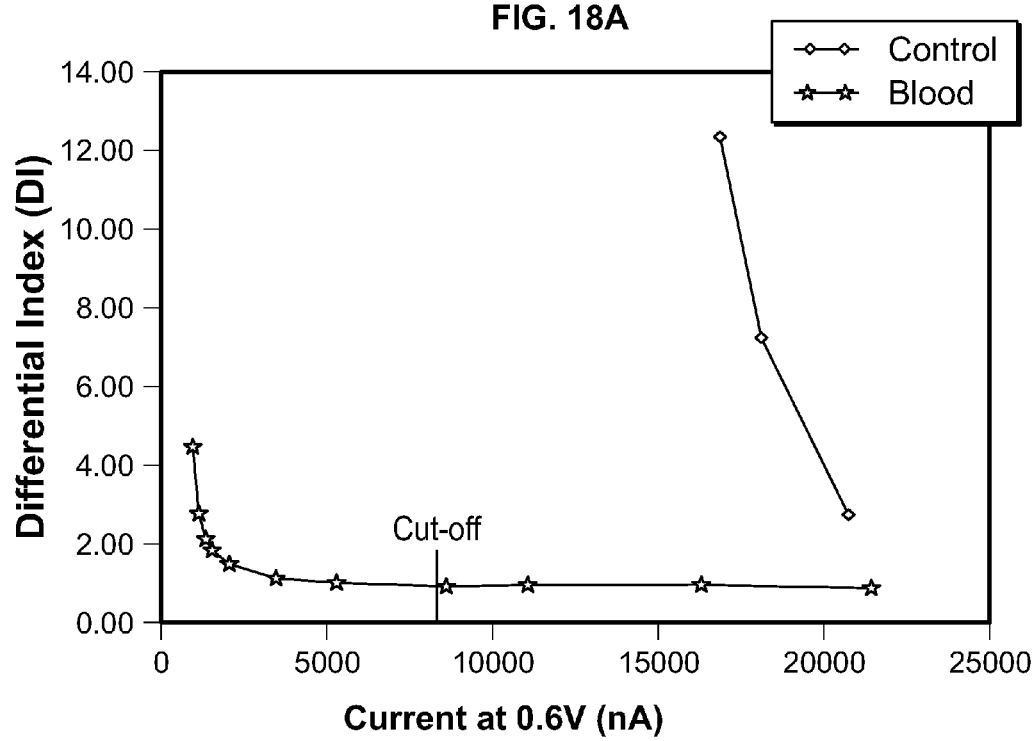

Referring to FIGS. 18A, 18B, using the same data, control solution and blood samples with different glucose concentrations were plotted. Specifically, the control solution included 8-anilino-1-napthalenesulfonic acid and the polymer polyvinyl sulfonic acid (PVS). The control solutions also included three different concentrations of glucose. The blood samples had 40% hematocrit with glucose concentrations that varied between 20 and 1,200 mg/dL.

In FIG. 18A, the differential indexes (DI) of the control solutions and the blood samples were plotted against the glucose (in mg/dL). As shown in FIG. 18A, at very low glucose concentrations levels in the blood, it may be difficult to use only the differential index (DI) to differentiate between a control solution and a blood solution. Referring to FIG. 18B, the control solution, has current values ($i_{high\ volt}$) well above 15,000 nA. Thus, if the current is less than a predetermined value (e.g., 12,000 nA), then a blood sample is being measured as shown in FIG. 18B. If the current is greater than 12,000 nA, then the DI is used as shown in FIG. 18A to determine if a control solution or a blood sample is being tested. At currents greater than 12,000 nA, the glucose concentrations of the blood samples are high (see FIG. 18A with the concentrations exceeding about 600 mg/dL). As shown in FIG. 18A, if the DI is greater than, for example, about 1.5 or 2.0, then the control solution is being tested. If the DI is less than about 1.5, then a blood sample is being tested since the DI values at high glucose concentrations are below this number.

Example 16

Figure 19:
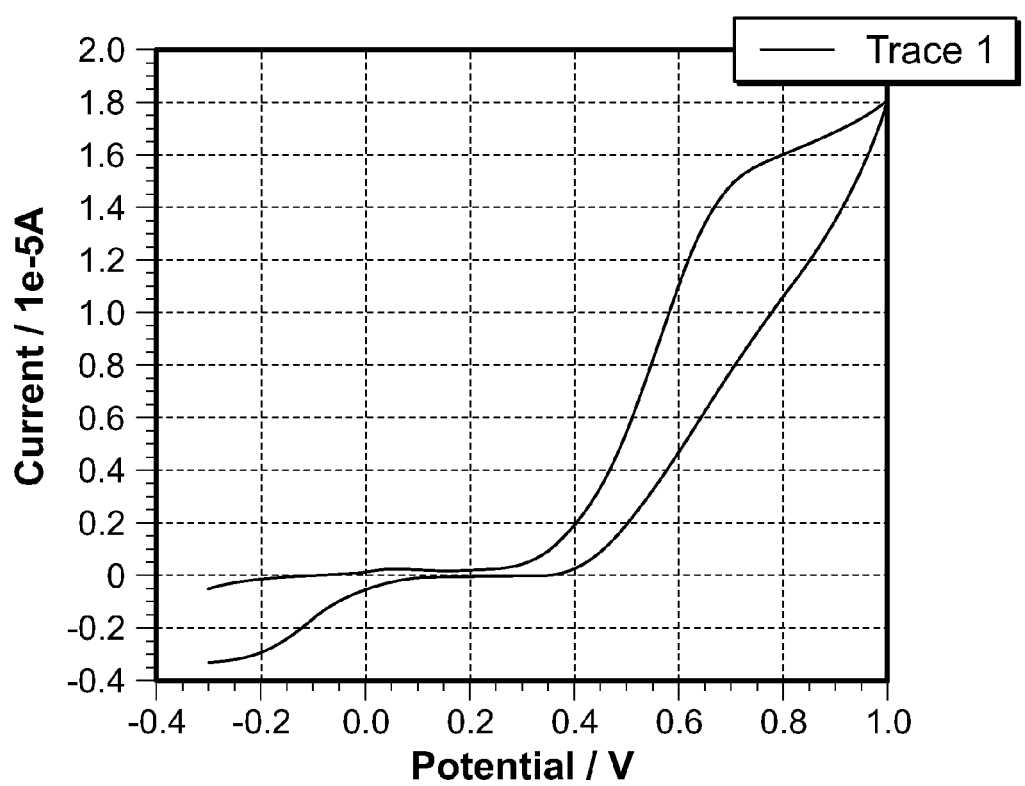
FIG. 19 is a cyclic voltammogram described in Example 16.

FIG. 19 shows the current plotted versus potential as the potential difference was cycled between –400 mV and +1,000 mV at 25 mV/sec using carbon electrodes. The testing was performed on an electrochemical work station of CH Instrument Co.

As shown in FIG. 19, Trace 1 represented the cyclic voltammogram of 50 mV MAOS N-ethyl-N-(2-hydroxy-3-sulfopropyl)-3,5-dimethylaniline, sodium salt (MAOS) and the mediator (2',5'-disulfophenylimino)-3H-phenothiazine. The sensor was manufactured with deposition of the mediator, enzyme, polymer and other ingredients. The large redox waves near 0 mV indicated the oxidation and reduction of the mediator in the sensor. The oxidation potential of the chemical species (MAOS) was about 400 to 700 mV higher than the mediator as shown in FIG. 19 by Trace 1. Thus, a low voltage at a potential of about 200 mV for the mediator and a high voltage at a potential in the range of about 400 to 700 mV for the control marker (MAOS) may be applied such that there is no overlap between the mediator's oxidation and the control marker's oxidation.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A method of using an electrochemical test sensor, the method comprising the acts of:
    introducing a fluid sample to the electrochemical test sensor;
    applying a pulse sequence to the fluid sample, the pulse sequence comprising at least two duty cycles within 180 seconds, at least one of the duty cycles having a first potential in a first excitation period and a first relaxation period, and after one of the duty cycles, providing a second potential to the sample, the second potential being greater than the first potential, the second potential being supplied after a second relaxation period, the second relaxation period being less than the first relaxation period;

measuring a first current at the first potential responsive to an analyte;

measuring a second current at the second potential responsive to the analyte; and determining whether the fluid sample is a control solution or an analyte-fluid test sample based on the measured first and second currents.

2. The method of claim 1 wherein at least one of the first and second relaxation periods uses an open circuit.

3. The method of claim 2 wherein the first and second relaxation periods use an open circuit.

4. The method of claim 1 wherein each of the duty cycles uses the first potential.

5. The method of claim 1 wherein the at least two duty cycles are from 3 to 18 duty cycles.

6. The method of claim 5 wherein the at least two duty cycles are from 3 to 10 duty cycles.

7. The method of claim 6 wherein the at least two duty cycles are performed in 30 seconds or less.

8. The method of claim 1 wherein the at least two duty cycles are 3 to 8 duty cycles and are performed in 3 to 16 seconds.

* * * * *